(12) United States Patent
Bodor

(10) Patent No.: US 7,691,811 B2
(45) Date of Patent: *Apr. 6, 2010

(54) TRANSPORTER-ENHANCED CORTICOSTEROID ACTIVITY AND METHODS AND COMPOSITIONS FOR TREATING DRY EYE

(76) Inventor: Nicholas S. Bodor, 10225 Collins Ave., Units 1002/1004, Bal Harbour, FL (US) 33154

( * ) Notice: Subject to any disclaimer, the term of this patent is extended or adjusted under 35 U.S.C. 154(b) by 0 days.

This patent is subject to a terminal disclaimer.

(21) Appl. No.: 11/943,264

(22) Filed: Nov. 20, 2007

(65) Prior Publication Data

US 2008/0194468 A1  Aug. 14, 2008

Related U.S. Application Data

(63) Continuation-in-part of application No. 11/802,403, filed on May 22, 2007.

(60) Provisional application No. 60/808,118, filed on May 25, 2006.

(51) Int. Cl.
A61K 38/00 (2006.01)
A01N 45/00 (2006.01)
A61K 31/56 (2006.01)

(52) U.S. Cl. .......................... 514/9; 514/170; 514/177; 514/179

(58) Field of Classification Search ............... 514/9, 514/170, 177, 179
See application file for complete search history.

(56) References Cited

U.S. PATENT DOCUMENTS

| | | | |
|---|---|---|---|
| 3,828,080 A | 8/1974 | Phillipps et al. | |
| 4,285,937 A | 8/1981 | Kalvoda | |
| 4,710,495 A | 12/1987 | Bodor | |
| 4,804,539 A | 2/1989 | Guo et al. | |
| 4,996,335 A | 2/1991 | Bodor | |
| 5,075,104 A | 12/1991 | Gressel et al. | |
| 5,278,151 A | 1/1994 | Korb et al. | |
| 5,294,607 A | 3/1994 | Glonek et al. | |
| 5,371,108 A | 12/1994 | Korb et al. | |
| 5,578,586 A | 11/1996 | Glonek et al. | |
| 5,916,550 A | 6/1999 | Inada et al. | |
| 5,981,517 A | 11/1999 | Bodor | |
| 6,153,607 A | 11/2000 | Pflugfelder et al. | |
| 6,368,616 B1 | 4/2002 | Doi | |
| 2002/0182185 A1* | 12/2002 | Wong | 424/93.7 |
| 2003/0008853 A1 | 1/2003 | Yanni et al. | |
| 2003/0109509 A1* | 6/2003 | Gamache et al. | 514/171 |
| 2005/0020551 A1 | 1/2005 | Bodor | |
| 2005/0026892 A1 | 2/2005 | Bodor | |
| 2005/0182039 A1 | 8/2005 | Meyering | |
| 2005/0222110 A1 | 10/2005 | Bartels | |
| 2006/0069075 A1 | 3/2006 | Gamache et al. | |
| 2006/0148686 A1 | 7/2006 | Xia et al. | |
| 2007/0105761 A1 | 5/2007 | Chappell et al. | |

FOREIGN PATENT DOCUMENTS

| | | | |
|---|---|---|---|
| GB | 1 384 372 | | 2/1975 |
| GB | 2079755 A | * | 1/1982 |
| WO | 97/42214 A1 | | 11/1997 |
| WO | 03/030893 A1 | | 4/2003 |
| WO | 2004/112800 A | | 12/2004 |

OTHER PUBLICATIONS

Bodor et. al., Pharmaceutical Research, 1992, Plenum Publishing Corp., 9, 1275-1278.*
P. Druzgala et al., "Soft Drugs-10. Blanching Activity and Receptor Binding Affinity of a New Type of Glucocorticoid: Loteprednol Etabonate", J. Steroid Biochem. Molec. Biol., vol. 38, No. 2, pp. 149-154, 1999, Pergamon Press plc, Great Britain.
Würthwein et al., "Lipophilicity and Receptor Affinity of Glucocorticoids", Pharm. Ztg. Wiss., Nr. 4-5/137, 1992, Govi-Verlag, Pharmazeutischer Verlag, Germany.
H. Derendorf, Ph.D., "Pharmacokinetics and pharmacodynamics of inhaled corticosteroids", J. Allergy Clin Immunol, vol. 101, No. 4, Part 2, pp. S440-S446, 1998, Elsevier Health, US.
Brattsand, "A Pharmacologist's View Based on Experiences from the Budesonide Project", Drug Development of Inhaled Steroids, Lung Biology in Health and Disease, vol. 163, pp. 3-32, 2002, Marcel Dekker, Inc., US.

(Continued)

Primary Examiner—Sreeni Padmanabhan
Assistant Examiner—Sarah Pihonak
(74) Attorney, Agent, or Firm—Buchanan Ingersoll & Rooney PC

(57) ABSTRACT

Methods and compositions for enhancing the activity and/or duration of action of loteprednol etabonate and other soft anti-inflammatory steroids of the haloalkyl 17α-alkoxycarbonyloxy-11β-hydroxyandrost-4-en-3-one-17β-carboxylate type and the corresponding $\Delta^{1,4}$-compounds are described. The enhancing agents have the formula:

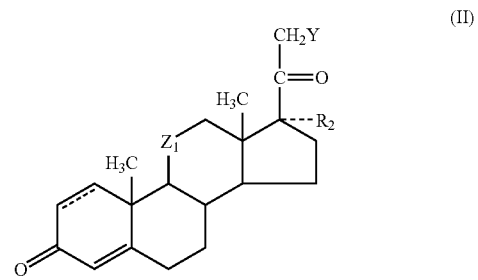

wherein $Z_1$ is carbonyl, β-hydroxymethylene or methylene; $R_2$ is H, —OH or —OCOR$_3$ wherein $R_3$ is $C_{1-5}$ alkyl; Y is —OH, —SH or —OCOR$_4$ wherein $R_4$ is $C_{1-5}$ alkyl, cyclopentylethyl or diethylaminoethyl; and the dotted line in ring A indicates that the 1,2-linkage is saturated or unsaturated. Ophthalmic administration in the treatment of dry eye is specifically targeted.

16 Claims, 2 Drawing Sheets

OTHER PUBLICATIONS

Wolff et al., "Nature of Steroid-Glucocorticoid Receptor Interactions: Thermodynamic Analysis of the Binding Reaction", Steroid-Glucocorticoid Receptor Interactions, Biochemistry, vol. 17, No. 16, pp. 3201-3208, 1978, American Chemical Society, US.

Ponec et al., "Glucocorticoids: Binding Affinity and Lipophilicity", Journal of Pharmaceutical Sciences, vol. 75, No. 10, pp. 973-975, 1986, American Pharmaceutical Association, US.

Derendorf et al., "Receptor-Based Pharmacokinetic-Pharmacodynamic Analysis of Corticosteroids", J. Clin Pharmcol, vol. 33, pp. 115-123, 1993, American College of Clinical Pharmacology, US.

Hammer et al., "Glucocorticoid receptor interactions with glucocorticoids: evaluation by molecular modeling and functional analysis of glucocorticoid receptor mutants", Steroids, vol. 68, pp. 329-339, 2003, Elsevier, US.

Dahlberg et al., "Correlation between Chemical Structure, Receptor Binding, and Biological Activity of Some Novel, Highly Active, 16α, 17α-Acetal-Substituted Glucocorticoids", Molecular Pharmacology, vol. 25, pp. 70-78, The American Society for Pharmacology, US.

Rohatagi et al., "Population Pharmacokinetics and Pharmacodynamics of Ciclesonide", J Clin Pharmacol, vol. 43, pp. 365-378, 2003, The American College of Clinical Pharmacology, US.

Belvisi et al., "Preclinical Profile of Ciclesonide, a Novel Corticosteroid for the Treatment of Asthma", J. Pharmacol. Exp. Ther., vol. 314, No. 2, pp. 568-574, 2005, The American Society for Pharmacology and Experimental Therapeutics, US.

Buchwald et al., "Soft glucocorticoid design: structural elements and physicochemical parameters determining receptor-binding affinity", Pharmazie, vol. 59, No. 5, pp. 396-404, 2004, Govi-Verlag Pharmazautischer Verlag, Germany.

Smith et al., "In vitro Glucocorticoid Receptor Binding and Transcriptional Activation by Topically Active Glucocorticoids", Arzneim-Forsch./Drug Res., vol. 48(II), No. 9, pp. 956-960, 1998, Editio Cantor Verlages, Germany.

Valotis et al., "Human Receptor Kinetics, Tissue Binding Affinity, and Stability of Mometasone Furoate", Journal of Pharmaceutical Sciences, vol. 93, No. 5, pp. 1337-1350, 2004, Wiley, US.

Issar et al., "Differences in the glucocorticoid to progesterone receptor selectivity of inhaled glucocorticoids", European Respiratory Journal, vol. 27, No. 3, pp. 511-516, 2006, European Respiratory Society, Switzerland.

Bodor et al., "Design and Devlopment of a Soft Corticosteroid, Loteprednol Etabonate", Inhaled Steroids in Asthma. Optimizing Effects in the Airways, Lung Biology in Health and Disease, vol. 163, pp. 541-564, 2002, Informa Healthcare, US.

Park et al., "Synthesis and pharmacological evaluations of new steroidal anti-inflammatory antedrugs: 9αFluoro-11β,17α,21-trihydroxy-3,20-dioxo-pregna-1,4-diene-16α-carboxylate(FP16CM) and its derivatives", Steroids, vol. 71, pp. 83-89, 2006, Elsevier, US.

Mager et al., "Quantitative Structure-Pharmacokinetic/Pharmacodynamic Relationships of Corticosteroids in Man", Journal of Pharmaceutical Sciences, vol. 91, No. 11, pp. 2441-2451, 2002, Wiley, US.

Cramer et al., "Comparative Molecular Field Analysis (CoMFA), 1, Effect of Shape on Binding of Steroids to Carrier Proteins", J. Am. Chem. Soc., vol. 110, pp. 5959-5967, 1988, American Chemical Society, US.

Good et al., "Structure-Activity Relationships from Molecular Similarity Matrices", J. Med. Chem., vol. 36, pp. 433-438, 1993, American Chemical Society, US.

Pfugfelder et al., "A Randomized, Double-Masked, Placebo-Controlled, Multicenter Comparison of Loteprednol Etabonate Ophthalmic Suspension, 0.5% and Placebo for Treatment of Keratoconjunctivitis Sicca in Patients with Delayed Tear Clearance", Am. J. Ophthalmol. 2004, 138(3), 444-457, published by Elsevier Science, New York, NY.

Optometric Management, Issue: Feb. 2005, "Isolate the Source: A protective steroid quiets inflammation—and changes the way doctors treat dry eye," accessed at http://www.optometric.com/article.aspx?article=71289 on Jul 12, 2007.

Parkinson, "Taking on Dry Eye", Ophthalmology Management, Issue: Feb. 2005, accessed at http://www.ophmanagement.com/article.aspx?article=86275 on Jul. 12, 2007.

Yang et al. "A clinical study of the efficacy of topical corticosteroids on dry eye", Journal of Zhejiang University, Science B, 2006, 7(8):675-678, published by Zhejiang University Press, Hangzhou, China.

Sheppard, "Dry-eye and blepharitis patients", EyeWorld, Supplement Aug. 7, 2006, accessed at http://www.eyeworld.org/ew-weeksupplementarticle.php?id=138 on Nov. 14, 2007.

Kabat, "6th Annual Dry Eye Report: Take Your Care Beyond the Surface", Optometric Study Center: Feb. 2005 http://www.revoptom.com/print.asp?page=osc/3248/lesson.htm on Nov. 14, 2007.

International Search Report and Written Opinion of the International Searching Authority dated Feb. 14, 2008 for PCT/US2007/012304, filed May 24, 2007, which is the PCT counterpart of parent U.S. Appl. No. 11/802,403.

Copending Bodor U.S. Appl. No. 11/802,403 filed May 22, 2007.

International Preliminary Report on Patentability dated Nov. 28, 2008, for PCT/US2007/012304.

* cited by examiner

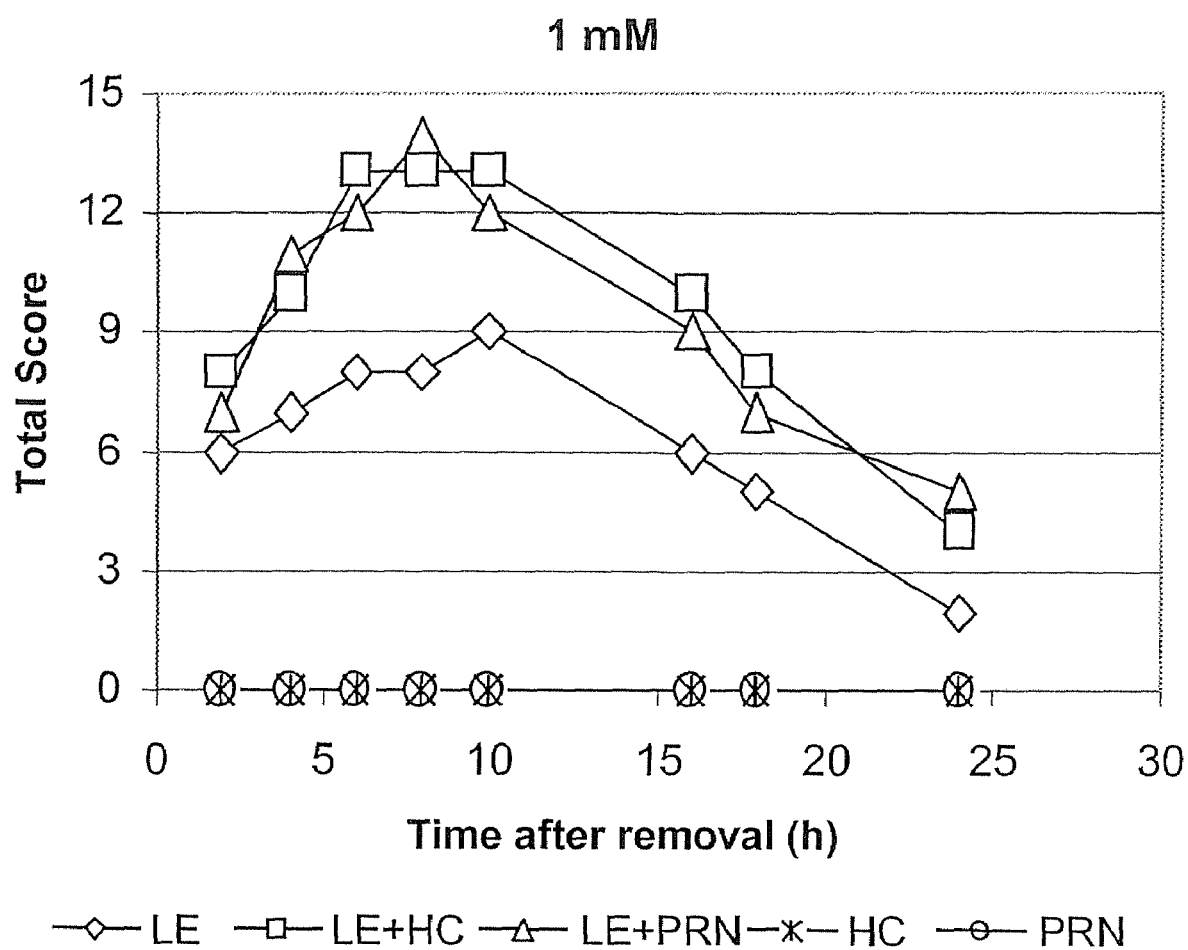

US 7,691,811 B2

TRANSPORTER-ENHANCED CORTICOSTEROID ACTIVITY AND METHODS AND COMPOSITIONS FOR TREATING DRY EYE

CROSS-REFERENCE TO EARLIER APPLICATIONS

This application is a continuation-in-part of earlier copending U.S. patent application Ser. No. 11/802,403, filed May 22, 2007, which claims benefit under 35 U.S.C. § 119(e) of U.S. Provisional Application No. 60/808,118, filed May 25, 2006, both earlier applications being incorporated by reference herein in their entireties and relied upon.

BACKGROUND OF THE INVENTION

1. Technical Field of the Invention

The invention relates to enhancing the activity and/or duration of action of particular anti-inflammatory steroids for topical or other local application, including ophthalmic application for the treatment of dry eye.

2. Background Art

Topical or other local application of potent glucocorticoids can produce severe toxic effects such as Cushingoid features, pituitary-adrenal suppression, skin atrophy, immunosuppression, weight gain and inhibition of wound healing. Other kinds of toxic responses, including allergies and cataracts, have resulted from long term use of drugs of this type.

Ophthalmic application of glucocorticosteroids presents additional problems The protective mechanisms built into the eye allow only small amounts of doses applied to the eye to reach the target sites within the eye; generally, over 90 percent of the total dose will find its way into the general circulation. This in turn leads to serious systemic side effects of the type described above. Moreover, there is a more serious and specific side effect when these drugs are used in the eye, which is an increase in intraocular pressure (IOP). Corticosteroid-induced chronic or acute glaucoma has in fact been reported since the early 1960's. Generally, the corticosteroid is needed only topically to control the inflammation. However, the absorbed steroid is responsible for the serious side effects noted above. It is believed that the effect of the corticosteroid, on the aqueous outflow pathway and adjacent, tissue glycosaminoglycans (GAG's) is important in the development of glucocorticoid-induced ocular hypertension.

The natural glucocorticosteroids and many of their marketed derivatives are $\Delta^4$ and $\Delta^{1,4}$ pregnenes having 21-hydroxy substituents. There are, however, a number of anti-inflammatory $\Delta^4$ and $\Delta^{1,4}$ androstenes described in the literature; note, for example, British Patent Specification No. 1,384,372; Phillipps et al. U.S. Pat. No. 3,828,080 and Kalvoda et al. U.S. Pat. No. 4,285,937.

In recent years, soft steroids have been developed in an effort to provide compounds having potent anti-inflammatory activity with minimal systemic activity. One series of soft steroids which is described as having potent an anti-inflammatory activity with minimal systemic activity consists of the 17α-carbonates of Bodor U.S. Pat. No. 4,996,335. These compounds include as preferred embodiments haloalkyl 17α-alkoxycarbonyloxy-11β-hydroxyandrost-4-en-3-one-17β-carboxylates and the corresponding $\Delta^{1,4}$ compounds, optionally bearing 6α- and/or 9α-fluorine and 16α- or 16β-methyl substituents. One of these compounds is chloromethyl 17α-ethoxycarbonyloxy-11β-hydroxyandrosta-1,4-dien-3-one-17β-carboxylate, also known as loteprednol etabonate. Loteprednol etabonate is presently marketed in the United States by Bausch & Lomb Pharmaceuticals, Inc. as Alrex® and Lotemax® and combined with tobramycin as Zylet® for ophthalmic use. Other uses of loteprednol etabonate are currently in clinical trials (for rhinitis and various dermatological conditions). Mention is also made of Bartels United States Patent Application Publication No. 2005/0222110, which describes the use of loteprednol etabonate itself for the treatment of dry eye, the contents of which is incorporated by reference herein in its entirety and relied upon; Pfugfelder et al.'s description of clinical trials utilizing 0.5% loteprednol etabonate suspension for treating keratoconjunctivitis sicca (Am. J. Opthalmol: 2004, 138(3), 444-457); and WO 03/030893, drawn to methods of treating dry eye by administering combinations of MUC-1 secretagogues, such as HETE derivatives, and anti-inflammatory steroids, one of which is loteprednol, this document also being incorporated by reference herein in its entirety and relied upon. See also Optometric Management, February 2005 in which Dr. Ron Melton is quoted as saying "Loteprednol 0.5% has revolutionalized the way we treat dry eye" (accessed at http://www.optometric.com/article.aspx?article=71289 on Jul. 12, 2007). Other publications relating to methods and compositions for treating dry eye utilizing loteprednol etabonate and compositions comprising it include Meyering U.S. Patent Appln. Publication No. 2005/0182039; Gamache et al. U.S. Patent Appln. Publication No. 2006/0069075; Xia et al. U.S. Patent Appln. Publication No. 2006/0148686 and Chappell et al. U.S. Patent Appln. Publication No. 2007/0105761, all incorporated by reference herein in their entireties and relied upon.

Despite the development of steroids having less systemic toxicity, however, there is a serious need for improvement in topical and other local applications. The newer, less toxic, locally/topically active compounds are more expensive to synthesize than the long-established compounds. Moreover, the most potent anti-inflammatory steroids are those which have substitution at the 6, 9 and/or 16-positions and thus also not only are farthest removed structurally from the natural corticosteroids but also have the greatest toxicity. Thus, there is a need for enhancing the activity or duration of action or both of the 17α-carbonate type soft androstenes which lack the 6-, 9- and/or 16-substitution pattern. Further, it would be desirable to allow these steroids to undergo easier metabolism and concentrate them at the desired site of action.

One of the major, inactive metabolites of hydrocortisone is cortienic acid, i.e. 11β,17α-dihydroxyandrost-4-en-3-one-17β-carboxylic acid Cortienic acid and the corresponding $\Delta^{1,4}$ acid have been previously described as synthetic intermediates useful in the preparation of the soft steroids described in Bodor U.S. Pat. Nos. 4,710,495 and 4,996,335. The 17β-methyl, ethyl and isopropyl esters of $\Delta^1$-cortienic acid have been described as putative inactive metabolites of the anti-inflammatory androstene derivatives of WO 97/42214 and Bodor U.S. Pat. No. 5,981,517. The '517 patent also describes the use of $\Delta^1$-cortienic acid as a competitor (with [3H]-triamcinolone acetonide as a tracer) for in vitro receptor-binding studies of the androstene derivatives of that patent and notes similar studies of loteprednol etabonate. Druzgala et al., J. Steroid Biochem. Mole. Biol., Vol. 38, No. 2, pp 149-154 (1991), reports earlier in vitro receptor binding studies of loteprednol etabonate and two putative metabolites, $\Delta^1$-cortienic acid and the corresponding 17α-ethyl carbonate, in a medium containing $10^{-5}$M cortienic acid as competitor, along with [3H]-triameimolone acetonide as tracer. Druzgala et al. further note that loteprednol itself is intrinsically active, whereas the putative metabolites are indeed inactive. Neither these acids nor their esters have been suggested as active ingredients for use in pharmaceutical compositions for the treatment of inflammation because they are not themselves active as anti-inflammatory agents. However, such inactive metabolites have been described as enhancing the anti-inflammatory activity and duration, of action of loteprednol etabonate and related soft steroids in Bodor United States Application Publication No. 2005/0026892A1, published Feb. 3, 2005. Such inactive metabolites have also been described as enhancing the anti-inflammatory activity and duration of action of selected other corticosteroids, for example, hydrocortisone; see Bodor United States Application Publication No. 2005/0020551 A1, published Jan. 27, 2005.

Nevertheless, there remains a need for alternate methods and compositions for enhancing the anti-inflammatory activity and duration of action of loteprednol etabonate and related soft, steroids.

SUMMARY AND OBJECTS OF THE INVENTION

It has now been found that hydrocortisone, prednisolone and related compounds enhance the topical or other local activity or duration of action of selected soft anti-inflammatory steroids such as loteprednol etabonate.

Thus, in one aspect, the present invention provides a pharmaceutical composition of matter comprising:
(1) a synergistic combination of:
(a) a compound having the formula:

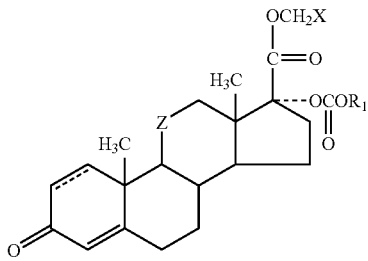

wherein:
$R_1$ is $C_1$-$C_7$alkyl;
Z is carbonyl or β-hydroxymethylene;
X is Cl or F;
and the dotted line in ring A indicates that the 1,2-linkage is saturated or unsaturated; and
(b) a compound having the formula:

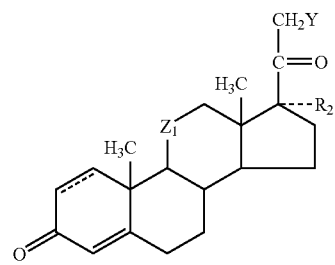

wherein:
$Z_1$ is carbonyl, β-hydroxymethylene or methylene;
$R_2$ is H, —OH or —OCOR$_3$ wherein $R_3$ is $C_1$-$C_5$ alkyl;
Y is OH, —SH or —OCOR$_4$, wherein $R_4$ is $C_1$-$C_5$ alkyl, cyclopentylethyl or diethylaminomethyl;

and the dotted line in ring A indicates that the 1,2-linkage is saturated or unsaturated;
and wherein the compound of formula (II) is present in an amount effective to enhance the anti-inflammatory activity or duration of action, or both, of said compound of formula (I); and
(2) a non-toxic pharmaceutically acceptable carrier therefor suitable for topical or other local application.

In another aspect, the invention provides a combination comprising (a) and (b) above, in a combined synergistic anti-inflammatory effective amount, the amount of (b) being sufficient to enhance the anti-inflammatory activity or duration of action, or both, of (a).

It is understood that the compositions and combinations of the present invention do not comprise, and the methods of the present invention likewise do not encompass the administration of, a compound of the formula:

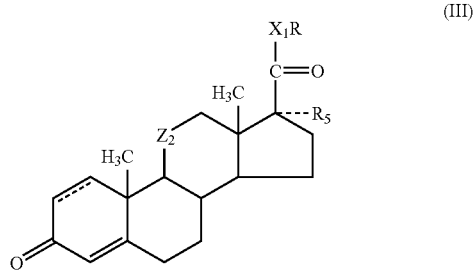

wherein:
R is H or $C_1$-$C_4$ alkyl;
$Z_2$ is carbonyl or β-hydroxymethylene;
$X_1$ is —O— or —S—;
$R_5$ is —OH, —OR$_6$, —OCOOR$_6$ or —OCOR$_7$ wherein $R_6$ is $C_1$-$C_4$ alkyl, and $R_7$ is $C_1$-$C_4$ alkyl, fluoromethyl or chloromethyl;
and the dotted line is defined as above;
with the proviso that when R is $C_1$-$C_4$ alkyl, then $R_5$ is —OH.

The compounds of formula (III) have been described as enhancers for the compounds of formula (I) in Bodor United States Application Publication No. 2005/0026892A1.

Therefore, in another aspect, the invention provides the compositions and combinations as described above but with the proviso that the composition or combination excludes a compound of formula (III), or with the proviso that, the composition or combination comprises (a) and (b) above as the only steroids in the composition; or with the proviso that the molar ratio of the compound of formula (II) to the compound of formula (I) is from about 2:1 to about 0.05:1 (preferably from about 1:1 to about 0.2:1, most preferably from about 1:1 to about 0.5:1). The indicated ratios represent preferred embodiments. It is to be noted that the compound of formula (II) is present in a subtherapeutic amount.

In still a further aspect, the compositions described above are ophthalmic compositions and the carrier is a non-toxic, ophthalmically acceptable one.

In another aspect, the present invention provides a pharmaceutical composition of matter comprising:
(a) an anti-inflammatory effective amount of a compound having formula (I) as defined above;
(b) an amount of a compound of formula (II) as defined above sufficient to enhance the anti-inflammatory activity or duration of action, or both, of said compound of formula (I); and (c) a non-toxic, pharmaceutically acceptable carrier suitable for topical or other local application;

with the optional provisos indicated hereinabove.

In yet another aspect, the invention provides a combination comprising:

(a) an anti-inflammatory effective amount of a compound having formula (I) as defined above; and (b) an amount of a compound of formula (II) as defined above sufficient to enhance the anti-inflammatory activity or duration of action, or both, of said compound of formula (I).

In a further aspect of the invention, there is provided a composition as defined in the preceding paragraph in which the composition is ophthalmic and the carrier is a non-toxic, ophthalmically acceptable one.

In yet another aspect, the present invention provides a method for enhancing the anti-inflammatory activity or duration of action, or both, of a compound having formula (I) as defined above following topical or other local administration of said compound to a warm-blooded animal to alleviate a topical or other localized (e.g. ophthalmic) inflammatory response, said method comprising topically or otherwise locally (e.g. ophthalmically) co-administering said compound to said animal with a synergistically effective amount of a compound having formula (II) as defined above, the amount of the compound of formula (II) being sufficient to enhance the anti-inflammatory activity or duration of action, or both, of said compound of formula (I). Preferably, the compounds are co-ad ministered in the form of one of the compositions of the invention defined above.

In still another aspect, the present invention provides a method for decreasing the in vivo transcortin binding of an anti-inflammatory steroid which binds to transcortin, and which is a compound having formula (I) as defined above, and for thus enhancing the anti-inflammatory activity or duration of action, or both, of said steroid following topical or other local administration of said steroid to a warm-blooded animal to alleviate a topical or other localized (e.g. ophthalmic) inflammatory response, said method comprising topically or otherwise locally (e.g. ophthalmically) co-administering said steroid to said animal with an amount of a compound having formula (II) above which is effective to decrease the in vivo transcortin binding of said steroid. Again, the compounds are preferably co-administered in the form of one of the compositions of the invention defined above.

Thus, the present invention provides a new use of a compound of formula (II) in the preparation of a medicament for treatment of topical and other local, inflammation, such as for treatment of ophthalmic inflammation; the compound of formula (II), while not itself having useful anti-inflammatory activity in the amount used, is employed, in accord with the present invention to enhance the activity of an anti-inflammatory steroid having transcortin binding activity, and having formula (I) above, by combining the compound of formula (II) with the active steroid of formula (I) in one of the compositions defined above.

In yet other aspects of the invention, there are provided combinations, compositions and methods for enhancing the activity or duration of action, or both, of the compound of formula (I) for use in the treatment of dry eye syndrome, a condition which is only partially inflammatory in nature.

BRIEF DESCRIPTION OF THE DRAWINGS

FIG. 2 is a graph of the variation in the effect of hydrocortisone (1 mM) and prednisolone (1 mM) on the vasoconstriction activity of loteprednol etabonate (1 mM) with time after removal, in hours.

DETAILED DESCRIPTION OF THE INVENTION

Figure 1:
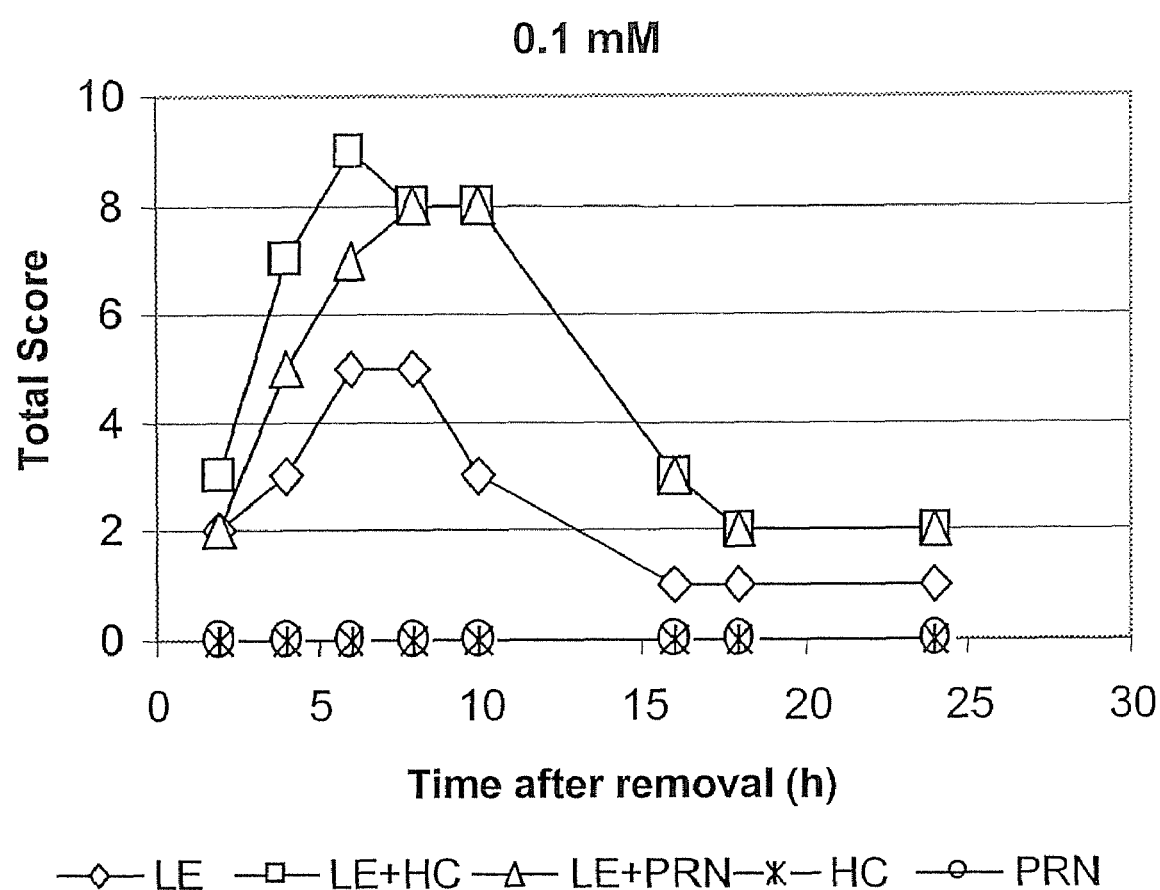
FIG. 1 is a graph of the variation in effect of hydrocortisone (0.1 mM) and prednisolone (0.1 mM) on the vasoconstriction activity of loteprednol etabonate (0.1 mM) with time after removal, in hours.

Throughout the instant specification and claims, the following definitions and general statements are applicable.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention. The basic and novel features herein are the provision of a combination of a compound of formula (I) with a compound of formula (II) which enhances the activity and/or duration of action of (I) for topical or other local application in the treatment of inflammation. In particular, the terms "consisting essentially of" or "consisting of" do not permit the inclusion of a compound of formula (III) above, i.e. an inactive metabolite enhancing agent, in the combinations, compositions and methods of the present invention.

The terms "consists of" and "consists" are closed terminology and allow only for the inclusion of the recited steps or features or components.

As used herein, the singular forms "a," "an" and "the" specifically also encompass the plural forms of the terms to which, they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

As used herein, the term "subtherapeutic amount" means an amount below that expected to have a therapeutic effect in a given combination/composition/method. A subtherapeutic amount can also be defined as an amount of the compound of formula (II) which is itself insufficient to have an anti-inflammatory activity, that is, insufficient to provoke or cause an anti-inflammatory response. Actual amounts vary with the particular compounds involved. For example, loteprednol etabonate of formula (I) has approximately 20 times the activity of hydrocortisone of formula (II). Therefore, a ratio of (II):(I) of 1:1 or 2:1 utilizes an amount of hydrocortisone (HC) which has only ¹/₁₀ or ¹/₂₀ the anti-inflammatory activity of the active ingredient loteprednol etabonate. Such an amount of FTC is effective as an enhancer of (I) but is not itself a large enough amount to be therapeutic. Rather, the amount is subtherapeutic.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed, McGraw Hill Companies Inc., New York (2001).

As used herein, "treating" means reducing, preventing, hindering or inhibiting the development of, controlling, alleviating and/or reversing the symptoms in the individual to which a combination or composition of the invention has been administered, as compared to the symptoms of an individual not being treated according to the invention. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods of the present invention are intended for use with any subject/patient that may experience the benefits of the methods of the invention. Thus, in accordance with the invention, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species.

The compounds of formula (II), while themselves much less active as glucocorticoids than the compounds of Formula (I) and most preferably used herein as synergistic in amounts lower than amounts considered therapeutically effective, are able to enhance the glucocorticoid activity and/or duration of glucocorticoid action of the compounds of formulas (I) by competing with them in vivo for transcortin binding sites. The addition of the compound of formula (II) hinders efflux away from the site of local administration (which is also the site of action) of the active anti-inflammatory compound of formula (I) by competing with the active compound for various in vivo systems which transport away from the site. This thus contributes to an increase in the amount of free active compound available at the desired site of action/administration or increases the time that the active compound remains at the site, or both. Further details of this mechanism of action are set forth later in this document.

With respect to the various groups encompassed, by the generic terms used here and throughout the specification, the definitions and explanations given below are applicable.

$R_1$ is a straight or branched-chain alkyl radical having 1 to 7 carbon atoms, preferably 1 to 4 carbon atoms, such as methyl, ethyl, n-propyl, isopropyl, isobutyl and n-butyl Z is carbonyl or β-hydroxymethylene, preferably β-hydroxymethylene.

X is chloro or fluoro, preferably chloro.

$Z_1$ is carbonyl or β-hydroxymethylene or methylene, preferably β-hydroxymethylene.

$R_2$ is hydroxy or —OCOR$_3$ wherein $R_3$ is straight or branched-chain alkyl having 1 to 5 carbon atoms, preferably 1 to 4 carbon atoms, such as methyl, ethyl, n-propyl and n-butyl. Preferably, $R_2$ is hydroxy, —OCOCH$_2$CH$_3$, —OCOCH$_2$CH$_2$CH$_3$ or —OCO(CH$_2$)$_3$CH$_3$.

Y is —OH —SH or —OCOR$_4$ wherein $R_4$ is straight or branched alkyl of 1 to 5 carbon atoms, cyclopentylethyl or diethylaminomethyl; Y is preferably —OH, —OCOCH$_3$, —OCOCH$_2$CH$_3$ or —OCOC(CH$_3$)$_3$.

The dotted line in formulas (I) and (II) indicates that the A-ring can have the $\Delta^4$ or $\Delta^{1,4}$ configuration. In the case of the compounds of formula (II), there is a preference for the structural variables, including the presence or absence of a 1,2-double bond, which correspond to those of corticosteroid, cortisol (hydrocortisone), 11-deoxycorticosterone, 11-deoxycortisol, prednisolone and Cortisol acetate, especially hydrocortisone and prednisolone. In the case of compounds of formula (I), it is most preferred that the structural variables, including the presence or absence of a 1,2-double bond, correspond to those of loteprednol etabonate.

The compounds of formula (I) above are described in Bodor U.S. Pat. No. 4,996,335, incorporated by reference herein in its entirety and relied upon. Specific compounds of formula (I) disclosed in that patent and representative of compounds of formula (I) for use herein include the following:

1. chloromethyl 17α-ethoxycarbonyloxy-11β-hydroxyandrosta-1,4-dien-3-one-17β-carboxylate, also known as loteprednol etabonate or LE;
2. chloromethyl 11β-hydroxy-17α-methoxycarbonyloxyandrost-4-en-3-one-17β-carboxylate;
3. chloromethyl 17α-ethoxycarbonyloxy-11β-hydroxyandrost-4-en-3-one-17β-carboxylate;
4. chloromethyl 17α-buloxycarbonyloxy-11β-hydroxyandrost-4-en-3-one-17β-carboxylate;
5. chloromethyl 11β-hydroxy-17α-isopropoxycarbonyloxyandrost-4-en-3-one-17β-carboxylate;
6. chloromethyl 11β-hydroxy-17α-isopropoxycarbonyloxyandrost-1,4-dien-3-one-17β-carboxylate;
7. chloromethyl 11β-hydroxy-17α-isobutoxycarbonyloxyandrost-4-en-3-one-17β-carboxylate;
8. chloromethyl 11β-hydroxy-17α-propoxycarbonyloxyandrost-4-en-3-one-17β-carboxylate;
9. fluoromethyl 11β-hydroxy-17α-isopropoxycarbonyloxyandrost-4-en-3-one-17β-carboxylate;

10. chloromethyl 11β-hydroxy-17α-n-propoxycarbonyloxyandrosta-1,4-dien-3-one-17β-carboxylate; and
11. chloromethyl 11β-hydroxy-17α-methoxycarbonyloxyandrosta-1,4-dien-3-one-17β-carboxylate.

An especially preferred compound of formula (I) for use in the present invention is chloromethyl 17α-ethoxycarbonyloxy-11β-hydroxyandrosta-1,4-dien-3-one-17β-carboxylate, or loteprednol etabonate. Loteprednol etabonate and other preferred compounds of formula (I) are those in which $R_1$ is methyl, ethyl, n-propyl, isopropyl, n-butyl or isobutyl, X is chloro, and Z is β-hydroxymethylene, most especially when the 1,2-linkage is unsaturated. These and other compounds of formula (I) can be prepared by methods described in the aforementioned '335 patent.

The compounds of formula (II) above are well-known anti-inflammatory steroids described in various patent and non-patent documents. Representative compounds include cortisone, cortisone acetate, hydrocortisone (cortisol), hydrocortisone acetate (cortisol acetate), hydrocortisone aceponate, hydrocortisone butyrate, cortisone 21-cyclopentanepropionate, hydrocortisone 21-cypionate, hydrocortisone valerate, prednisolone, prednisolone acetate, prednisolone tebutate (21-tert-butylacetate), prednisolone 21-pivalate (21-trimethylacetate), prednisolamate (prednisolone 21-diethylaminoacetate), prednival (prednisolone 17-valerate), prednisone, prednisone 21-acetate, corticosterone, tixocortol, corticosterone 21-acetate, hydrocortamate, 11-deoxycorticosterone, 11-deoxycortisol (11-deoxyhydrocortisone), prednicarbate and hydrocortisone tebutate (hydrocortisone 21-tert-butyl-acetate). The structures of these compounds are shown in the following TABLE 1 below.

TABLE 1

| Compound of Formula (II) | $Z_1$ | Δ | $R_2$ | Y |
|---|---|---|---|---|
| cortisone | C=O | 4 | —OH | —OH |
| cortisone acetate | C=O | 4 | —OH | —OCOCH$_3$ |
| hydrocortisone (cortisol) | CH(OH) | 4 | —OH | —OH |
| hydrocortisone acetate (cortisol acetate) | CH(OH) | 4 | —OH | —OCOCH$_3$ |
| hydrocortisone aceponate | CH(OH) | 4 | —OCOCH$_2$CH$_3$ | —OCOCH$_3$ |
| hydrocortisone butyrate | CH(OH) | 4 | —OCOCH$_2$CH$_2$CH$_3$ | OH |
| cortisone 21-cyclopentane-propionate | C=O | 4 | —OH | —OCOCH$_2$CH$_2$-(cyclopentyl) |
| hydrocortisone cypionate | CH(OH) | 4 | —OH | ----OCOCH$_2$CH$_2$-(cyclopentyl) |
| hydrocortisone valerate | CH(OH) | 4 | —OCO(CH$_2$)$_3$CH$_3$ | —OH |
| prednisolone | CH(OH) | 1,4 | —OH | —OH |
| prednisolamate | CH(OH) | 1,4 | —OH | —OCOCH$_2$N(C$_2$H$_5$)$_2$ |

TABLE 1-continued

| Compound of Formula (II) | $Z_1$ | Δ | $R_2$ | Y |
|---|---|---|---|---|
| prednisolone acetate | >C(H)(OH) | 1, 4 | —OH | —OCOCH$_3$ |
| prednisolone tebutate | >C(H)(OH) | 1, 4 | —OH | —OCOCH$_2$C(CH$_3$)$_3$ |
| prednisolone 21-pivalate | >C(H)(OH) | 1, 4 | —OH | —OCOC(CH$_3$)$_3$ |
| Prednival | >C(H)(OH) | 1, 4 | —OCO(CH$_2$)$_3$CH$_3$ | —OH |
| prednisone | >C=O | 1, 4 | —OH | —OH |
| prednisone 21-acetate | >C=O | 1, 4 | —OH | —OCOCH$_3$ |
| corticosterone | >C(H)(OH) | 4 | —H | —OH |
| tixocortol | >C(H)(OH) | 4 | —OH | —SH |
| corticosterone 21-acetate | >C(H)(OH) | 4 | —H | —OCOCH$_3$ |
| hydrocortamate | >C(H)(OH) | 4 | —OH | —OCOCH$_2$N(C$_2$H$_5$)$_2$ |
| prednicarbate | >C(H)(OH) | 1, 4 | —OCOC$_2$H$_5$ | —OCOC$_2$H$_5$ |
| hydrocortisone tebutate | >C(H)(OH) | 4 | —OH | —OCOCH$_2$C(CH$_3$)$_3$ |
| 11-deoxy-corticosterone | >C(H)(H) | 4 | —H | —OH |
| 11-deoxycortisol | >C(H)(H) | 4 | —OH | —OH |

In the compositions and methods of the present invention, the enhancing agent of formula (II) and compound of formula (I) are generally used in a molar ratio of from about 2:1 to about 0.05:1 (preferably from about 1:1 to about 0.2:1, even more preferably from about 1:1 to about 0.5:1), that is, from about 0-05 to about 2 moles (preferably from about 0.2 to about 1 mole) of the formula (II) compound for each mole of compound of formula (I). In situations in which the molecular weight of the formula (II) compound is similar to that of the selected compound of formula (I), a weight/weight ratio of from about 2:1 to about 0.05:1 (preferably 0.2:1 to 1:1, approximately) will closely approximate the about 2:1 to about 0.05:1 (preferably about 0.2:1 to about 1:1) molar ratio and can be used instead for ease in formulating pharmaceutical formulations. Indeed, even when the molecular weight of the compound of formula (I) is 10-20% greater than that of the formula (II) compound, the about 2:1 to about 0.05:1 (II):(I) (preferably about 0.2:1 to about 1:1) weight ratio can be conveniently employed.

The rationale for the present combination of compounds of formula (I) and (II) is as follows:

There are two major specific receptors important for corticosteroid activity. One is the glucocorticoid receptor (GCR or GR), which quantitates the relative intrinsic activity, as the relative strengths for binding to this receptor. The GCR is ubiquitous, that is, it is found in essentially every cell, so systemic steroids (either by systemic administration or by distribution from local application) will produce systemic effects, many of them unwanted. This receptor (GCR) is responsible for the ACTIVITY. Of course, by definition, the more potent, glucocorticoids replace weaker ones on this specific receptor. Actually, this is the basis of measuring their relative activities.

The second receptor involved in many of the glucocorticoids is the so-called Corticosteroid Binding Globulin (CBG), which is also called transcortin. This again specifically binds corticosteroids and transports them in the general circulatory system to different sites. This is a specific binding, but one that is not responsible for activity.

The present inventor has found that the relative binding to the two specific receptors, GCR and CBG, do not run parallel. Some compounds with weak activity (low GCR binding), bind strongly to transcortin (CBG) Interestingly, however, while all corticosteroids bind to GCR, only a handful of them bind effectively to transcortin The following table shows the GR (GCR) relative binding affinities of a number of representative glucocorticosteroids for the GCR. As can be seen from this table, compounds such as hydrocortisone and its esters and prednisolone, which are representative of the compounds of formula (II), have much lower GCR values than loteprednol etabonate, a representative compound of formula (I).

RBA of Representative Glucocorticoids for the GCR (GR)

| Compound | Formula | logP | rBA[a] | Ref |
|---|---|---|---|---|
| Beclomethasone | $C_{22}H_{29}Cl_{01}O_{05}$ | $2.36^b$ | 76 | [1] |
| Beclomethasone 17-monopropionate | $C_{25}H_{33}Cl_{01}O_{06}$ | 3.63 | 1440 | [2, 3] |
| Beclomethasone dipropionate | $C_{28}H_{37}Cl_{01}O_{07}$ | 4.40 | 140 | [2, 3] |
| Betamethasone | $C_{22}H_{29}F_{01}O_{05}$ | 1.94 | 79 | [4-7] |
| Budesonide, 22R | $C_{25}H_{34}O_{06}$ | 3.24 | 1120 | [8] |
| Budesonide, 22S | $C_{25}H_{34}O_{06}$ | 3.24 | 420 | [8] |
| Ciclesonide | $C_{32}H_{44}O_{07}$ | $5.14^b$ | 15 | [9, 10] |
| Ciclesonide, act. metab. | $C_{28}H_{38}O_{06}$ | $3.87^b$ | 1681 | [9, 10] |
| Clobetasol propionate | $C_{25}H_{32}Cl_{01}F_{01}O_{05}$ | 3.83 | 6300 | [7] |
| Corticosterone | $C_{21}H_{30}O_{04}$ | 1.94 | 35 | [4, 5, 8] |
| Dexamethasone | $C_{22}H_{29}F_{01}O_{05}$ | 1.83 | 100 | |
| Etiprednol dicloacetate (BNP-166) | $C_{24}H_{30}Cl_{02}O_{06}$ | $4.44^b$ | 200 | [11] |
| Flunisolide | $C_{24}H_{31}F_{01}O_{06}$ | 2.28 | 165 | [2, 3] |
| Fluticasone propionate | $C_{25}H_{31}F_{03}O_{05}S_{01}$ | 4.20 | 1796 | [1-3, 10, 12-14] |
| Hydrocortisone (cortisol) | $C_{21}H_{30}O_{05}$ | 1.61 | 10 | [4, 6, 8] |
| Hydrocortisone 17-acetate | $C_{23}H_{32}O_{06}$ | 2.30 | 41 | [5] |
| Hydrocortisone 17-butyrate | $C_{25}H_{36}O_{06}$ | 3.18 | 95 | [5] |
| Hydrocortisone 17-propionate | $C_{24}H_{34}O_{06}$ | 2.70 | 79 | [5] |
| Loteprednol etabonate | $C_{24}H_{31}Cl_{01}O_{07}$ | 3.03 | 150 | [15, 16] |
| Mometasone | $C_{22}H_{28}Cl_{02}O_{04}$ | $3.11^b$ | 88 | [14] |
| Mometasone furoate | $C_{27}H_{30}Cl_{02}O_{06}$ | $4.53^b$ | 1833 | [3, 7, 12-14] |
| Prednisolone | $C_{21}H_{28}O_{05}$ | 1.62 | 19 | [4, 6, 7, 17] |
| Triamcinolone | $C_{21}H_{27}F_{01}O_{06}$ | 1.16 | 45 | [5, 18] |
| Triamcinolone acetonide | $C_{24}H_{31}F_{01}O_{06}$ | 2.53 | 270 | [1, 4-6, 8, 12] |

[a]Relative receptor binding affinities are for the glucocorticoid receptor and are relative to dexamethasone as reference ($rRBA_{Dex} = 100$). Average of all values was used if multiple values were available.
[b]Calculated logP is given where no logP is reported in literature

REFERENCES

[1] Würthwein, G.; Rehder, S.; Rohdewald, P. Lipophilicity and receptor affinity of glucocorticoids. *Pharm. Ztg. Wiss.*, 1992, 4-5/137, 161-167.

[2] Derendorf, H.; Hochhaus, G.; Mcibohm, B.; Möllmann, H.; Barth, J. Pharmacokinetics and pharmacodynamics of inhaled corticosteroids. *J. Allergy Clin. Immunol*, 1998, 101, S440-S446.

[3] Brattsand, R. A. pharmacologist's view based on experiences from the budesonide project. In *Inhaled Steroids in Asthma Optimizing Effects in the Airways*; Schleimer, R. P., O'Byrne, P. M., Szefler, S. J., Brattsand, R., Eds.; Marcel Dekker: New York, 2002; Lung Biology in Health and Disease, vol. 163, Vol. pp. 3-32.

[4] Wolff, M. E.; Baxter, J. D.; Kollman, P. A.; Lee, D. L.;: Kuntz, I. D.; Bloom, E.; Matulich, D. T.; Morris, J. Nature of steroid-glucocorticoid receptor interactions: thermodynamic analysis of the binding reaction. *Biochemistry*, 1978, 17, 3201-3208.

[5] Ponec, M.; Kempenaar, J.; Shroot, B.; Caron, J.-C. Glucocorticoids: binding affinity and lipophilicity *J. Pharm Sci*, 1986, 75, 973-975.

[6] Derendorf, H.; Hochhaus, G.; Möllmann, H.; Barth, J.; Krieg, M.; Tunn, S.; Möllmann, C. Receptor-based pharmacokinetic-pharmacodynamic analysis of corticosteroids. *J. Clin. Pharmacol*, 1993, 35, 115-123.

[7] Hammer, S.; Spika, L.; Sippl, W.; Jessen, G.; Kleuser, B.; Höltje, H.-D.; Schäfer-Korting, M. Glucocorticoid receptor interactions with glucocorticoids: evaluation by molecular modeling and functional analysis of glucocorticoid receptor mutants. *Steroids,* 2003, 68, 329-339.

[8] Dahlberg, E.; Thalén, A.; Brattsand, R.; Gustafsson, J.-Å.; Johansson, U.; Roempke, K.; Saartok, T. Correlation between chemical structure, receptor binding, and biological activity of some novel, highly active, 16α,17α-acetal-substituted glucocorticoids. *Mol. Pharmacol.,* 1984, 25, 70-78.

[9] Rohatagi, S.; Arya, V.; Zech, K.; Nave, R.; Hochhaus, G.; Jensen, K.; Barrett, J. S. Population pharmacokinetics and pharmacodynamics of ciclesonide. *J. Clin. Pharmacol.,* 2003, 43, 365-378.

[10] Belvisi, M. G.; Bundschuh, D. S.; Stoeck, M.; Wicks, S.; Underwood, S.; Battram, C. H.; Haddad el, B.; Webber, S. E.; Foster, M. L. Preclinical profile of ciclesonide, a novel corticosteroid for the treatment of asthma. *J. Pharmacol. Exp. Ther.* 2005, 314, 568-574.

[11] Buchwald, P.; Bodor, N. Soft glucocorticoid design: structural elements and physicochemical parameters determining receptor-binding affinity. *Pharmazie,* 2004, 59, 396-404.

[12] Smith, C. L.; Kreutner, W. In vitro glucocorticoid receptor binding and transcriptional activation by topically active glucocorticoids. *Arzneim.-Forsch./Drug Res.,* 1998, 48 (II), 956-960.

[13] Valotis, A.; Neukam, K.; Elert, O.; Högger, P. Human receptor kinetics, tissue binding affinity, and stability of mometasone furoate. *J. Pharm Sci.,* 2004, 93, 1337-1350.

[14] Issar, M.; Sahasranaman, S.; Buchwald, P.; Hochhaus, G. Differences in the glucocorticoid to progesterone receptor selectivity of inhaled glucocorticoids. *Eur. Respir. J.,* 2006, 27, 511-516.

[15] Druzgala, P.; Hochhaus, G.; Bodor, N. Soft drugs. 10. Blanching activity and receptor binding affinity of a new type of glucocorticoid: loteprednol etabonate. *J. Steroid Biochem,* 1991, 38, 149-154.

[16] Bodor, N.; Buchwald, P. Design and development of a soft corticosteroid, loteprednol etabonate. In *Inhaled Steroids in Asthma Optimizing Effects in the Airways*; Sehleimer, R. P., O'Byrne, P. M., Szefler, S. J., Brattsand, R., Eds.; Marcel Dekker: New York, 2002; Lung Biology in Health and Disease, vol. 163, Vol. pp. 541-564.

[17] Park, K.-K,; Ko, D.-H.; You. Z.; Heiman, A. S.; Lee, H. J. Synthesis and pharmacological evaluations of new steroidal anti-inflammatory antedrugs: 9α-Fluoro-11β,17α, 21-trihydroxy-3,20-dioxo-pregna-1,4-diene-16α-carboxylate (FP16CM) and its derivatives. *Steroids,* 2006, 71, 83-89.

[18] Mager, D. E.; Jusko, W. J. Quantitative structure-pharmacokinetic/pharmacodynamic relationships of corticosteroids in man, *J. Pharm. Sci.,* 2002, 91, 2441-2451.

While the glucocorticoid receptor (GR, or GCR) is the main receptor that mediates glucocorticoid activity and is a major determinant of therapeutic potential which is related to, for example, the clinical efficacy of inhaled glucocorticoids, to side-effects such as cortisol suppression, to immunosuppressive potency, etc., transcortin or CBG is a transport/cargo protein which binds biologically active steroids with much higher affinity and specificity than other plasma proteins and is a major detriment of steroid bioavailability. CBG binding influences activity because only the unbound fraction of the corticosteroid exercises activity.

The following table shows the CBG binding affinities of a number of steroids which appear in the scientific literature. Those in Class 1 have the highest binding activity; of the Class 1 members, those which are glucocorticoids, that is anti-inflammatory steroids, are of the greatest interest to the present invention.

| GBC Binding Affinities | | |
|---|---|---|
| Compound | Log 1/K | Class |
| aldosterone | −6.279 | 2 |
| androstanediol | −5.000 | 3 |
| 5-androstenediol | −5.000 | 3 |
| 4-androstenedione | −5.763 | 3 |
| androsterone | −5.613 | 3 |
| corticosterone | −7.881 | 1 |
| cortisol (hydrocortisone) | −7.881 | 1 |
| cortisone | −6.892 | 2 |
| dehydroepiandrosterone | −5.000 | 3 |
| 11-deoxycorticosterone | −7.653 | 1 |
| 11-deoxycortisol | −7.881 | 1 |
| dihydrotestosterone | −5.919 | 2 |
| estradiol | −5.000 | 3 |
| estriol | −5.000 | 3 |
| estrone | −5.000 | 3 |
| etiocholanolone | −5.225 | 3 |
| pregnenolone | −5.225 | 3 |
| 17α-hydroxypregnenolone | −5.000 | 3 |
| progesterone | −7.380 | 1 |
| 17α-hydroxyprogesterone | −7.740 | 1 |
| testosterone | −6.724 | 2 |
| prednisolone | −7.512 | 1 |
| cortisolacetat | −7.553 | 1 |
| 4-pregnene-3,11,20-trione | −6.779 | 2 |
| epicorticosterone | −7.200 | 1 |
| 19-nortestosterone | −6.144 | 2 |
| 16α,17α-dihydroxyprogesterone | −6.247 | 2 |
| 16α-methylprogesterone | −7.120 | 1 |
| 19-norprogesterone | −6.817 | 2 |
| 2α-methylcortisol | −7.688 | 1 |
| 2α-methyl-9α-fluoro-cortisol | −5.797 | 2 |

GBC binding activity data after. *J. Am. Chem, Soc.* 1988 110, 5959 and *J. Med Chem.* 1993, 36, 433. Activity classes 1: high, 2: intermediate, 3: low.

Experiments were undertaken to determine specific CBG (transcortin) binding values for a number of glucocorticoids and $IC_{50}$-values were calculated.

Experimental procedure: Venous blood was collected from healthy volunteers into heparin-containing tubes (5 Us/100 ml serum) and cells were separated from plasma by centrifugation (1500 g for 15 min). The plasma was treated with charcoal suspension (Harvey et al., J. Steroid Biochem 7: 55, 1976) in order to remove endogenous steroids. Charcoal-treated plasma was diluted 100-fold with binding buffer (10 mM Tris-HCl; 2 mM DTT (dithiotreitol); 1.5 mM EDTA; 0.02 M $Na_2MoO_4$; 10% Glycerol; pH 7.4) and was stored aliquoted at −80° C., Binding of $^3$H-cortisol (69.0 Ci/mmol, Amersham Biosciences), was determined using the charcoal adsorption procedure, as described previously by Korenmann (*Steroids* 13: 163, 1976). Briefly: aliquots (0.3 ml) of diluted serum were added to assay tubes containing 3 nM $^3$H-cortisol alone or containing various concentrations of unlabeled steroid competitors. Non-specific binding was defined using 500-fold excess of unlabeled cortisol. The assay ingredients were mixed and the tubes were incubated for 1 hour on ice. At the end of the incubation, 0.2 ml of charcoal suspension (0.5% Norit A and 0.05% BSA) was added to each tube. The tubes were briefly agitated and incubated for an additional 10 min at 0° C. They were then centrifuged for 10 min at 15 000 g, and the same aliquots from the clear supernatants were quantitatively decanted into counting vials and combined with 3 ml of toluene-based scintillation fluid. Radioactivity was determined by a Wallac LKB 1410 radiospektro-fluorim-éter. Specific binding and $IC_{50}$-values were calculated.

Results: are shown in Table 2.

TABLE 2

Binding of different corticosteroids to transcortin ($IC_{50}$ nM)

| Compound | $IC_{50}$-values (nM) average ± SEM (n) |
|---|---|
| Cortisol | 69 ± 8 (12) |
| Prednisolone | 6.7 ± 1.6 (3) |
| Prednisone | 36 ± 11 (3) |
| Etiprednol Dicloacetate | 4502 ± 973 (4) |
| Loteprednol etabonate | 272 ± 27 (4) |

TABLE 2-continued

Binding of different corticosteroids to transcortin (IC$_{50}$ nM)

| Compound | | IC$_{50}$-values (nM) average ± SEM (n) |
|---|---|---|
| Cortienic acid (CA) GYKI-24805 | 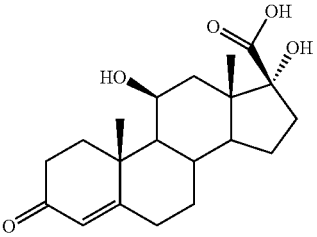 | 117 ± 49 (4) |
| CA-Me GYKI-25806 | 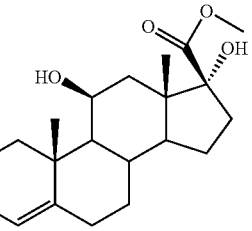 | 5.9 ± 1.4 (4) |
| Δ1-CA GYKI-24762 | 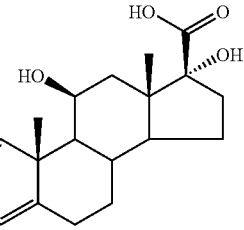 | 52 ± 10 (3) |
| Δ1-CA-Me GYKI-24776 | 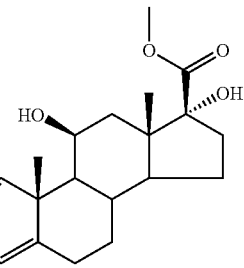 | 31 ± 11 (3) |

The present inventor has observed that GR and CBG affinities do not run in parallel. The following table graphically illustrates this point.

GR versus CBG Affinities
GR and CBG binding affinities do not run in parallel

| Compound | GR Est. IC$_{50}$ (nM) | CBG Est. IC$_{50}$ (nM) |
|---|---|---|
| prednisolone (PR) | 30 | 7 |
| Δ$^1$-CA, methyl ester (Δ$^1$-CA, Me) | >1000 | 30 |
| Δ$^1$-cortienic acid (Δ$^1$-CA) | >1000 | 50 |
| cortisol (hydrocortisone, HC) | 67 | 70 |
| cortienic acid (CA) | >1000 | 120 |
| loteprednol etabonate (LE) | 4 | 270 |
| budesonide (BUD) | 0.9 | >10000 |
| ciclesonide, act. met. (CIC-AM) | 0.5 | >10000 |
| fluticasone propionate (FP) | 0.4 | >10000 |
| mometasone furoate (MF) | 0.4 | >10000 |

Bodor, N.; Kuruez, I. 2006, unpublished results.
Note:
GRs were calculated from RBAs.

Glucocorticoid activity, as represented by GR affinity, has thus been found not to parallel transcortin binding, as represented by CBG affinity. The present invention makes use of this lack of parallel. Since lower IC$_{50}$'s's represent greater activity, the most active glucocorticoids have the lowest GR Est. IC$_{50}$'s in the above table, while those binding most strongly to transcortin have the lowest CBG Est. IC$_{50}$'s. Hydrocortisone, the natural corticosteroid, and related compounds (such as the hydrocortisone esters) bind very well to transcortin, although they are weak glucocorticoids. It appears that the prednisolone class (with one additional double bond in the C1-C2 position), binds even more strongly. These compounds are strong transcortin binders, significantly better than the much more potent loteprednol. Substituents such as 6-fluoro, 6-methyl, 9-fluoro etc. very much reduce transcortin binding, so such compounds cannot be similarly enhanced.

While the combination with cortienic acid (CA), $\Delta^1$ CA and esters are effective CBG binders, although totally inactive, such are new, virtually unstudied compounds. The current invention, however, selects combinations of potent GCR binding steroids, which have weak CBG binding, with the reverse properties, that is with weak GC-s which are strong transcortin binders. For example, the relatively weak hydrocortisone (HC), or weaker cortisone, also prednisone and prednisolone (PRN), which have much higher CBG binding properties, in combination with the much more potent loteprednol etabonate (LE), yield a significant, enhancement, of the local (skin, nose, lung, colon, etc.) activity, by virtue of effecting transport, away of LE, without producing airy local or systemic contribution to the desired GC activity. The studies below clearly demonstrate the enhancement of the activity (extent and time) of LE on human skin, when combined with equivalent amounts of HC or PRN. HC or PRN alone do not yield airy detectable activity. See Table 3 and FIGS. 1 and 2.

Thus, the pharmacological activity of a glucocorticoid that binds to CBG can be strongly enhanced and its duration of action prolonged by mixing it with another steroid that has stronger affinity for CBG. If the second compound has no strong GR activity, it is not expected to cause any unexpected GR-related side effects. For example, the activity of the soft steroid loteprednol etabonate, which binds to CBG, is strongly increased and prolonged by combining it with hydrocortisone or prednisolone.

The compounds of formulas (I) and (II) can be combined with suitable non-toxic pharmaceutically acceptable earners to provide pharmaceutical compositions for use in the treatment of topical or other localized inflammation. Obviously, in view of their lack of systemic activity, compositions containing the compounds of formula (I) are not intended for treatment of conditions where systemic adrenocortical therapy is indicated, e.g., adrenocortical insufficiency. As examples of inflammatory conditions which can be treated with pharmaceutical compositions containing the combination of a compound of formula (I) and a compound of formula (II) and one or more pharmaceutical carriers, the following can be mentioned: dermatological disorders such as atopic dermatitis, acne, psoriasis or contact dermatitis; allergic states such as bronchial asthma; ophthalmic and otic diseases involving acute and chronic allergic and inflammatory reactions (for example, ophthalmic inflammatory conditions such as blepharitis, conjunctivitis, episcleritis, scleritis, keratitis, anterior uveitis and sympathetic ophthalmia, including ophthalmic conditions which are only partially inflammatory in nature including in particular "dry eye" syndrome, also known as keratoconjunctivitis sicca (KCS), and ear inflammations of the outer and middle ear as well as inflammation of the inner ear, for example Meniere's Disease, injected or instilled into the inner ear through the ear drum analogous to the current use of dexamethasone); respiratory diseases; inflammations of the mouth, gums and/or throat, such as gingivitis or oral aphtha; inflammations of the nasal mucosa, for example, those caused by allergies; inflammations of the upper and lower intestines, such as Crohn's disease and ulcerative colitis; inflammations associated with arthritis; and anorectal inflammation, pruritus and pain associated with hemorrhoids, proctitis, cryptitis, fissures, postoperative pain and pruritus am. Such compositions may also be applied locally as a prophylactic measure against the inflammation and tissue rejection which arise in connection with transplants.

Obviously, the choice of carrier(s) and dosage forms will vary with the particular condition for which the composition is to be administered.

Examples of various types of preparations for topical/local administration include ointments, gels, lotions, creams, powders, drops (e.g., eye or ear or nose drops), sprays (e.g., for the nose or throat), suppositories, retention enemas, chewable or suckable tablets or pellets (e.g., for the treatment of aphthous ulcers) aerosols, tablets and capsules, and solutions (e.g., mouthwashes for treatment of inflammation of the oral cavity, especially the mouth or gums).

Ointments and creams or gels may, for example, be formulated with an aqueous or oily base with the addition of suitable thickening and/or gelling agents and/or glycols. Such base may thus, for example, include water and/or an oil such as liquid paraffin or a vegetable oil such as arachis oil or castor oil, or a glycolic solvent such as propylene glycol or 1,3-butanediol. Thickening agents which may be used according to the nature of the base include soft paraffin, aluminum stearate, cetostearyl alcohol, polyethylene glycols, woolfat, hydrogenated lanolin and beeswax and/or glyceryl monostearate and/or non-ionic emulsifying agents.

The solubility of the steroids in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following, namely, emulsifying agents, dispersing agents, suspending agents, thickening agents, solvents, coloring agents and perfumes.

Powders may be formed with the aid of any suitable powder base e.g., tale, lactose or starch.

Drops may be formulated with an aqueous base also comprising one or more dispersing agents, suspending agents or solubilizing agents, etc.

Spray compositions may, for example, be formulated as aerosols with the use of a suitable propellant, e.g., dichlorodifluoromethane or trichlorofluoromethane.

Nebulized or powdered formulations may be prepared for oral inhalation in the treatment of asthma, as is well-known in the art.

Solutions and suspensions may be prepared for oral or rectal administration for use in the treatment of inflammations of the intestines, for example, as described in more detail in the examples hereinafter. Moreover, tablets, capsules and other oral dosage forms may be used, for example, in the treatment of Crohn's disease, provided that, they are formulated for delayed release (such as three hours after administration) to protect the compounds of formulas (I) and (II) from gastric juice and to thus allow them to reach the target site, such as the duodenum, before dissolving.

Parenteral/injectable formulations may be prepared for direct injection into the joints in the treatment of arthritis in accord with methods well-known to those skilled in the art of parenteral formulations.

The combinations of the present invention can be incorporated into nanospheres or microspheres in a variety of dosage forms (oral, topical, inhalation, etc.) to provide sustained/ controlled release of the compounds of formulas (I) and (II) to treat various inflammatory conditions and/or in the case of dermal or transdermal patches containing the combinations so incorporated, to provide anti-inflammatory relief for dermatological irritations caused by patches themselves, for example, as a result of sensitivity to the adhesive used or as a result of long-term use of occlusive products. In a dermal or transdermal patch, the combination of the invention is present for its local or dermal action. Other active ingredients may be present for their systemic action in a transdermal patch or their local action in a dermal patch. Thus, for example, the combination of the invention can be included in nanospheres or microspheres incorporated into patches for smoking cessation treatment, e.g., nicotine patches, for treatment of cardiovascular conditions, e.g., nitroglycerin patches; for treatment of menopausal conditions, e.g., patches containing an estrogen such as estradiol, or an estrogen such as estradiol in combination with a progestin; vapor patches for treatment of congestion and related respiratory conditions; patches for treating asthma, such as tulobuterol patches; patches for pain management containing analgesics; patches containing other dermatological agents such as antibacterials/antibiotics or antifungals; patches containing testosterone or anti-anxiety agents or drugs for treating attention deficit disorder (ADD). The sustained/controlled release properties of nanosphere or microsphere technology for the instant combinations can also be advantageously utilized in conjunction with devices which need to be in continuous contact with the body, such as insulin pumps and continuous glucose monitors and ports, again to provide anti-inflammatory relief for the dermatological conditions which result from long-term use of adhesive and/or occlusive products. Nanosphere/microsphere technology can also be used for sustained delivery (over a period of months or years) of the combination of the invention from intravitreal implants, to reduce and/or inhibit inflammation of the retina and to thus treat retinopathy, or such sustained delivery of the combination from cardiac stents to reduce and/or inhibit inflammation at their locus, Nanospheres may, by way of example only, range from 100 nm to 800 nm, while microspheres may be exemplified by ranges of 2 μm to 4 μm, or even 40 μm to 60 μm or 220 μm to 280 μm. Other technologies may of course be utilized to control dermal delivery of the instant combination.

The amount of active ingredient and enhancer in the compositions according to the invention will vary with the precise compounds used, the type of formulation prepared and the particular condition for which the composition is to be administered. The formulation will generally contain from about 0.0001 to about 5.0% by weight of the compound of formula (I). Topical preparations will generally contain 0.0001 to 2.5%, preferably 0.01 to 0.5% of active compound, and will be administered once daily, or as needed. The identity and amount of active compound will determine the amount of formula (II) compound utilized therewith, in keeping with the desired molar or weight ratios discussed above. Also, generally speaking, the compounds of formulas (I) and (II) can be incorporated into topical and other local compositions formulated substantially as are such presently available types of compositions containing known glucocorticosteroids, with the amount of compound of formula (I) varying according to its potency.

The compositions of the invention may be formulated to include other active compounds known to be useful in combination with anti-inflammatory steroids, for example, antifungal, antibacterial, antibiotic and local anaesthetic agents, for example, clotrimazole, clioquinol (iodochlorhydroxyquin), iodoquinol, polymyxin B sulfate, neomycin sulfate, tobramycin, sulfacetamide sodium, gentamicin, thonzonium bromide, colistin sulfate and pramoxine hydrochloride. The steroids of formulas (I) and (II) may be combined with more than one of these additional active agents when appropriate, for example, with a combination of polymyxin B sulfate and neomycin sulfate.

The anti-inflammatory activity of the compounds of formula (I) is well-known from the aforementioned Bodor U.S. Pat. No. 4,996,335 and the scientific literature; as noted earlier, one of these compounds, loteprednol etabonate, is currently marketed in the United States for ophthalmic administration as an anti-inflammatory agent. The marketed Alrex® 0.2% sterile ophthalmic suspension is indicated for the temporary relief of signs and symptoms of seasonal allergic conjunctivitis while the marketed Lotomax® 0.5% sterile ophthalmic suspension is indicated for the treatment of steroid-responsive inflammatory conditions of the palpebral and bulbar conjunctiva, cornea and anterior segment of the globe such as allergic conjunctivitis, acne rosacea, superficial punctate keratitis, herpes zoster keratitis, iritis, cyclitis, selected infective conjunctivitides, to reduce edema and inflammation. Lotomax® has more recently been found particularly useful in treating dry eye syndrome. A third marketed product (Zylet®) is an ophthalmic suspension of loteprednol etabonate 0.5% and tobramycin 0.3% and is indicated for steroid-responsive inflammatory ocular conditions for which a corticosteroid is indicated and where superficial bacterial ocular infection or risk thereof exists and where the inherent risk of steroid use in certain infective conjunctivitides is accepted to obtain a diminution in edema and inflammation. The Zylet® combination has been found particularly useful in treating patients with blepharitis, bacterial conjunctivitis, peripheral ulcerative keratitis and ocular trauma. Other formulations for local administration for a variety of conditions are in clinical trials.

The combination and compositions of the present invention are particularly useful for treating the conditions for which the compound of formula (I), especially loteprednol etabonate, has been found useful, for example, as Alrex®, Lotomax® and Zylet® compositions. Because of the enhancement afforded by the presence of the compound of formula (II), lower dosages of loteprednol etabonate can often be used to produce the same or better results.

The combinations of the present invention have undergone human vasoconstriction, or blanching, testing. Such testing gives a reliable indication of local anti-inflammatory/glucocorticoid activity. In the present case, it has been used to show that representative enhancing agents of formula (II) are inactive alone at the tested levels, that a representative compound of formula (I) is active alone at the tested levels, and that administering a compound of formula (II) with a compound of formula (I) enhances the anti-inflammatory activity or duration of action or both of the representative formula (I) compound.

Human Vasoconstriction Testing

Objective

The objective of this study is to evaluate the increased vasoconstriction effects of loteprednol etabonate (LE) by hydrocortisone (HC) or prednisolone (PRN).

Methodology

Solutions of LE, HC and PRN (0.1 or 1 mM) alone, or mixtures of LE and HC (0.1+0.1 mM, or 1+1 mM), or LE and PRN (0.1+0.1 mM, or 1+1 mM) were prepared with a vehicle containing absolute ethanol and propylene glycol (9:1). The resulting mixtures (20 μl) were loaded on the circular paper disc (7 mm diameter), that were attached to a water impervious adhesive film (3M). After evaporation of ethanol (20 min), the films were applied to the forearms of human volunteers for 4 hours. Subsequently, the vasoconstriction reaction was read and judged by the appearance of pallor at various time intervals after the removal of the discs and films. The grading scale was as follows: 0, normal skin; 1, slight pallor; 2, pallor with at least two corners outlined; 3, even pallor with a clear outlined of the application sites; 4, very intense pallor. Due to the relatively high variations in response between the volunteers, a total score of 4 tests at each time point was taken for the activity evaluation.

Results and Discussion

Human vasoconstriction test has been used as an index of percutaneous absorption, activity and bioavailability of glucocorticoids. In this study, the addition of HC, and PRN were investigated to evaluate their effects on the activity of LE. Based on the previous findings, both HC and PRN are easily bound to transcortin receptors, and the pharmacological activity of corticosteroids was not correlated to the transcortin bindings, the following hypothesis was established by the inventor: when applied together with LE, HC or PRN occupy the transcortin receptor sites that are readily available to LE, resulting in more LE molecules bound to the glucocorticoid receptors, thus enhancing the local pharmacological activity of LE.

The results in the Table 3 and FIGS. 1 and 2 indicate that by itself, LE showed good vasoconstriction activity, and both HC and PRN showed no activity at the concentration range of 0.1 to 1 mM. The activity of LE was greatly increased by addition, of the same amounts of HC or PRN (60-80% increase after co-administration of 0.1 mM, and 60-75% increase after co-administration of 1 mM). Since the vasoconstriction activity of HC was 500 times less than (50 mM HC vs. 0.1 mM LE tested), and PRN was 250 times less than (25 mM PRN vs. 0.1 mM LE tested) that of LE as previously reported, the increased vasoconstriction activity of LE by HC and PRN can be considered as due, not to the glucocorticoid receptor bindings of HC and PRN, but to the increased LE-glucocorticoid receptor bindings. These results have thus confirmed the hypothesis.

TABLE 3

Vasoconstriction activity (total score of 4 tests).[1,2,3]

| Concentration | Time after removal, hr | | | | | | | |
|---|---|---|---|---|---|---|---|---|
| mM | 2 | 4 | 6 | 8 | 10 | 16 | 18 | 24 |
| 0.1 mM | | | | | | | | |
| LE | 2 | 3 | 5 | 5 | 3 | 1 | 1 | 1 |
| LE + HC | 3 | 7 | 9 | 8 | 8 | 3 | 2 | 2 |
| LE + PRN | 2 | 5 | 7 | 8 | 8 | 3 | 2 | 2 |
| HC | 0 | 0 | 0 | 0 | 0 | 0 | 0 | 0 |
| PRN | 0 | 0 | 0 | 0 | 0 | 0 | 0 | 0 |
| 1 mM | | | | | | | | |
| LE | 6 | 7 | 8 | 8 | 9 | 6 | 5 | 2 |
| LE + HC | 8 | 10 | 13 | 13 | 13 | 10 | 8 | 4 |
| LE + PRN | 7 | 11 | 12 | 14 | 12 | 9 | 7 | 5 |
| HC | 0 | 0 | 0 | 0 | 0 | 0 | 0 | 0 |
| PRN | 0 | 0 | 0 | 0 | 0 | 0 | 0 | 0 |

[1]Compounds were dissolved in ethanol/propylene glycol (9/1) solution, and 20 µl of the mixtures were applied to circular patches (7 mm diameter). The patches were applied to the forearms of the human volunteers, and covered with a water impervious film for 4 hours. The intensity of vasoconstriction was judged at various time periods after the patches are removed.
[2]The grading scale was as follows: 0, normal skin; 1, slight pallor; 2, pallor with at least two corners outlined; 3, even pallor with a clear outlined of the application sites; 4, very intense pallor.
[3]The total scores at each time period were taken due to the large variations between the individual responses.

Conclusions

The results obtained indicate that the activity and duration of action, of a potent and CBG-binding steroid of formula (I) can be significantly enhanced by the addition of another stronger CBG-bound, but lower GR-activity steroid of formula (II) by affecting the concentration of unbound steroid and the trans port-away processes.

The following Examples illustrate numerous formulations suitable for administering the combinations of a compound of formula (I) and a compound of formula (II) to treat various kinds of local inflammatory conditions. These formulations are merely illustrative and not limitative of the remainder of the specification and claims in any way whatsoever.

In these Examples, percentages are by weight unless otherwise noted.

EXAMPLE 1

A nasal suspension is prepared having the following composition:

| NASAL SUSPENSION | |
|---|---|
| Loteprednol etabonate (LE) | 0.5 to 1.0 g |
| Hydrocortisone | 0.5 to 1.0 g |
| | (in 1:1 ratio to LE) |
| Concentrated glycerin | 2.6 g |
| Polysorbate 80 | 0.2 g |
| Microcrystalline cellulose carmellose sodium | 2.0 to 3.0 g |
| Citric acid | q.s. |
| Benzalkonium chloride | 0.005 g |
| Purified water q.s. | 100 g (pH 5.5) |

The suspension can be prepared in accord with the procedure described in Doi U.S. Pat. No. 6,368,616 B1 of Apr. 9, 2002, incorporated by reference herein in its entirety and relied upon, except for the addition of hydrocortisone, which can occur at the same time as the addition of loteprednol etabonate.

Alternatively, from 0.1 to 0.5 g of hydrocortisone may be used instead of the 0.5 to 1.0 g amount, listed above.

EXAMPLE 2

A nasal suspension is prepared having the following composition:

| NASAL SUSPENSION | |
|---|---|
| Loteprednol etabonate | 0.5 g |
| Prednisolone | 0.1 to 0.5 g |
| Propylene glycol | 2.0 g |
| Polyoxyethylene hydrogenated castor oil 60 | 0.2 g |
| Microcrystalline cellulose carmellose sodium | 3.0 g |
| Phosphoric acid | q.s. |
| Benzethonium chloride | 0.005 g |
| Purified water q.s. | 100 g (pH 5.5) |

The suspension can be prepared in accord with, the procedure of the aforementioned '616 patent, except for the addition of prednisolone, which can occur at the same time as the addition of loteprednol etabonate.

The foregoing nasal formulations can be modified as described, in the '616 patent.

The following formulations can be prepared using routine production procedures for formulations of these types.

EXAMPLE 3

An eye drop suspension is prepared having the following composition:

| EYE DROP SUSPENSION | |
|---|---|
| Loteprednol etabonate | 0.5 g |
| Prednisolone | 0.1 to 0.5 g |
| ε-Aminocaproic acid | 0.1 g |
| Tyloxapol | 0.3 g |
| Polyvinylpyrrolidone (intrinsic viscosity = 30) | 0.6 g |
| Sodium edetate | 0.01 g |
| Benzalkonium chloride (10 w/v %) | 0.05 mL |
| Hydrochloric acid | q.s. |
| Sterilized pure water | q.s 100 ml |
| pH | 5.53 |

0.05 to 0.1 mL of this suspension can be distilled into the eye 3 to 10 times daily for the treatment of dry eye and other ophthalmic conditions. Alternatively, 0.2 g of loteprednol etabonate and 0.1 to 0.2 g of prednisolone can be used in this suspension formulation for various ophthalmic conditions, including dry eye.

This suspension formulation can be modified as described in Inada et al U.S. Pat. No. 5,916,550, of Jun. 29, 1999, incorporated by reference herein in its entirety and relied upon, except for the addition of prednisolone at the time of loteprednol etabonate incorporation, to provide other aqueous suspensions for use in the eye or nose which do not undergo pH depression even after prolonged storage.

EXAMPLE 4

An ointment is prepared having the following composition:

| OINTMENT | |
|---|---|
| Compound of formula (I) e.g. loteprednol etabonate | 0.20% w/w |
| Compound of formula (II), e.g. prednisone | 0.10 to 0.20% w/w |
| Liquid paraffin | 10.0% ww |
| White soft paraffin | 89.5% w/w |

EXAMPLE 5

An aphthous ulcer pellet is prepared, having the following composition:

| APHTHOUS ULCER PELLET | |
|---|---|
| Compound of formula (I), e.g. loteprednol etabonate | 0.20 mg |
| Compound of formula (II), e.g. corticosterone | 0.05 to 0.3 mg |
| Lactose | 69.0 mg |
| *Acacia* | 3.00 mg |
| Magnesium stearate | 0.75 mg |

EXAMPLE 6

A retention enema is prepared having the following composition:

| RETENTION ENEMA | |
|---|---|
| Compound of formula (I), e.g. loteprednol etabonate | 0.01% w/v |
| Compound of formula. (II), e.g. hydrocortisone | 0.01% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |

EXAMPLE 7

Eye drops are prepared having the following composition:

| EYE DROPS | |
|---|---|
| Compound of formula (I), e.g. loteprednol etabonate | 0.2% w/v |
| Compound of formula (II), e.g. prednisolone acetate | 0.10 to 0.20% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

These eye drops are of particular use in the treatment of dry eye syndrome as well as in the treatment of other various inflammatory ophthalmic conditions.

EXAMPLE 8

A dermal ointment is prepared having the following composition:

| DERMAL OINTMENT | |
|---|---|
| Compound of formula (I), e.g. loteprednol etabonate | 0.2% w/w |
| Compound of formula (II), e.g. hydrocortisone | 0.2% w/w |
| Liquid Paraffin | 10.0% w/w |
| White soft paraffin | 88.8% w/w |

EXAMPLE 9

An aphthous ulcer pellet is prepared having the following composition:

| APHTHOUS ULCER PELLET | |
|---|---|
| Compound of formula (I), e.g. loteprednol etabonate | 0.15 mg |
| Compound of formula (II), e.g. hydrocortisone | 0.5 to 0.15 mg |
| Lactose | 60.25 mg |
| *Acacia* | 3.0 mg |
| Magnesium sterate | 0.75 mg |

EXAMPLE 10

A retention enema is prepared having the following composition:

| RETENTION ENEMA | |
| --- | --- |
| Compound of formula (I), e.g. loteprednol etabonate | 0.1% w/v |
| Compound of formula (II), e.g. hydrocortisone acetate | 0.1% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |

EXAMPLE 11

Eye drops are prepared having the following composition:

| EYE DROPS | |
| --- | --- |
| Compound of formula (I), e.g. loteprednol etabonate | 0.2% w/v |
| Compound of formula (II), e.g. prednisolone | 0.1 to 0.2% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

These eye drops are of particular interest in the treatment of dry eye syndrome.

EXAMPLE 12

Eye drops are prepared having the following composition:

| EYE DROPS | |
| --- | --- |
| Compound of formula (I), e.g. loteprednol etabonate | 0.5% w/v |
| Compound of formula (II), e.g. hydrocortisone | 0.2 to 0.5% w/v |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 volumes |

The ingredients listed above are combined, then the pH is checked and, if necessary, adjusted to 5.0-5.5 by basifying with sodium hydroxide or acidifying with hydrochloric acid.

These eye drops are useful in the treatment of dry eye syndrome.

Alternatively, 0.2% w/v of loteprednol etabonate and 0.1 to 0.2% w/v hydrocortisone or other compound of formula (II) can be used in this suspension formulation for various ophthalmic conditions, including dry eye.

EXAMPLE 13

An eye drop preparation especially adapted for treatment of dry eye is prepared as follows:

| Phase I | |
| --- | --- |
| Carbopol 934P NF (acrylic acid-based polymer) | 0.25 g |
| Purified Water | 99.75 g |
| Phase II | |
| Propylene Glycol | 5.0 g |
| EDTA | 0.1 mg |
| Loteprednol Etabonate | 20 to 50 g |
| Hydrocortisone or Prednisolone | 20 to 50 g, in 1:1 ratio with loteprednol etabonate |
| Cyclosporine | 5.0 g |

Five parts of Phase II are mixed with 20 parts of Phase I for 15 minutes, then the pH is adjusted to 6.2-6.4 using IN NaOH.

EXAMPLE 14

| | |
| --- | --- |
| Povidone | 1.00% w/w |
| HAP (30%) | 0.05% w/w |
| Glycerin | 3.00% w/w |
| Propylene Glycol | 3.00% w/w |
| Loteprednol Etabonate (LE) | 0.20-0.50% w/w |
| Hydrocortisone or Prednisolone or other compound of formula (II) | 0.20-0.50% w/w (in 1:1 ratio to LE) |
| Cyclosporine | 0.10% w/w |
| Tyloxapol | 0.25% w/w |
| Alexidine 2 HCl | 1-2 ppm |

This formulation is especially useful in the treatment of dry eye.

EXAMPLE 15

| | |
| --- | --- |
| Povidone | 1.50% w/w |
| HAP (30%) | 0.05% w/w |
| Glycerin | 3.00% w/w |
| Propylene Glycol | 3.00% w/w |
| Loteprednol Etabonate (LE) | 0.20-0.5% w/w |
| (Compound of formula (II), e.g. | 0.20-0.5% w/w |
| Hydrocortisone or Prednisolone | (in 1:1 ratio to LE) |
| Cyclosporine | 0.10% w/w |
| Tyloxapol | 0.25% w/w |
| Alexidine 2HCl | 1-2 ppm |

This formulation is designed for dry eye treatment

Yet other compositions of the invention can be conveniently formulated using known techniques Thus, for example, an inhalation formulation suitable for use in the treatment of asthma can be prepared as a metered-dose aerosol unit containing a representative compound of formula (I) such as loteprednol etabonate and a representative compound of formula (II) such as hydrocortisone, prednisolone, prednisone or corticosterone, according to procedures well-known to those skilled in the art of pharmaceutical formulations. Such an aerosol unit may contain a microcrystalline suspension of loteprednol etabonate and one of the aforementioned compounds of formula (II) in a (II):(I) weight ratio of from 0.5:1 or 0.2:1 to 1:1 in suitable propellants (e.g.

trichlorofluoromethane and dichlorodifluoromethane and dichlorotetrafluoroethane), with oleic acid, sorbitan trioleate or other suitable dispersing agent. Each unit typically contains 1-10 milligrams of the aforesaid loteprednol etabonate, approximately 5-50 micrograms of which are increased at each actuation Another example of a pharmaceutical composition according to the invention is a foam suitable for treatment of a wide variety of inflammatory anorectal disorders, to be applied anally or perianally, comprising 0.1% or 0.5% of a compound of formula (I) such, as loteprednol etabonate and 0.05% or 0.5%, respectively, of hydrocortisone or prednisolone, and 1% of a local anaesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellants. Alternatively, 0.2% or 1.0%) of hydrocortisone or prednisolone may be employed Yet another pharmaceutical formulation according to the invention is a solution or suspension suitable for use as a retention enema, a single dose of which typically contains 40-80 milligrams of a compound of formula (I) such as loteprednol etabonate and from 0.1 to 1 times that amount of a compound of formula (II), preferably hydrocortisone or prednisolone, together with sodium chloride, polysorbate 80 and 1 to 6 ounces of water (the water being added shortly before use). The suspension can be administered as a retention enema or by continuous drip several times weekly in the treatment of ulcerative colitis.

Another exemplary formulation is a sterile, multiple dose antibiotic and steroid combination suspension for topical ophthalmic use. Each mL of suspension contains: as active ingredients, tobramycin 0.3% (3 mg) and loteprednol etabonate 0.5% (5 mg); as synergist, hydrocortisone 0.1 to 0.5% (1 to 5 mg); as preservative, benzalkonium chloride 0.01%; and as inactives tyloxapol, edetate disodium, sodium chloride, hydroxyethyl cellulose, sodium sulfate, sulfuric acid and/or sodium hydroxide (to adjust pH) and purified water.

Another example of an antibiotic/steroid combination for topical ophthalmic use contains 0.5% loteprednol etabonate, 0.1 to 0.5% hydrocortisone or prednisolone, and 0.3% tobramycin together with edetate disodium, glycerin, povidone, purified water, tyloxapol and 0.01% benzalkonium chloride as preservative. Each mL contains 5 mg loteprednol etabonate, 1-5 mg hydrocortisone or prednisolone and 3 mg tobramycin. Sulfuric acid and/or sodium hydroxide may be added to adjust the pH to 5.7 to 5.9 and achieve isotonicity.

Another example is a sterile, multiple dose antibiotic and steroid combination ointment for topical ophthalmic use. Each gram of ointment contains: as active ingredients, tobramycin 0.3% (3 mg) and loteprednol etabonate 0.2% (0.2 mg); as synergist, prednisolone acetate 0.05% to 0.1% (0.5 to 1 mg); as preservative, chlorobutanol 0.5%; and as inactives, mineral oil and white petrolatum.

Yet another exemplary formulation is an ophthalmic anti-infective/anti-inflammatory sterile suspension containing: as active ingredients, sulfacetamide sodium 10% and loteprednol etabonate (microfine suspension) 0.5%; as synergist, prednisone 0.1 to 0.2%; as preservative, benzalkonium chloride (0.004%); as inactives, polyvinyl alcohol 1.4%, polysorbate 80, edetate disodium, dibasic sodium phosphate, monobasic potassium phosphate, sodium thiosulfate, hydrochloric acid and/or sodium hydroxide to adjust the pH, and purified water. A similar composition may be formulated for otic administration.

Another ophthalmic ointment containing an antibacterial and a corticosteroid is exemplified by a sterile ointment containing: as actives, sulfacetamide sodium 10% and loteprednol etabonate, 0.2%; as synergist, hydrocortisone, 0.05% to 0.2%; as preservative, phenylmercuric acetate (0.0008%); and as inactives, mineral oil, white petrolatum, and petrolatum and lanolin alcohol.

Another example of a sterile ophthalmic formulation is a topical anti-inflammatory/anti-infective suspension containing, as active ingredients, loteprednol etabonate (microfine suspension) 0.5%, neomycin sulfate equivalent to 0.35% neomycin base, polymyxin B sulfate 10,000 units/mL; as synergist, prednisone, 0.10 to 0.5%; as preservative, thimerosal 0.001%; and as inactive ingredients, polyvinyl alcohol 1.4%), polysorbate 80, propylene glycol, sodium acetate and purified water.

Yet another illustrative sterile ophthalmic suspension which is a topical anti-inflammatory/anti-infective combination product contains: as active ingredients, gentamicin sulfate equivalent to 0.3% gentamicin base and loteprednol etabonate (microfine suspension) 0.5%); as synergist, corticosterone, 0.2 to 0.5%; as preservative, benzalkonium chloride 0.005%; as inactive ingredients, polyvinyl alcohol 1.4%, edetate disodium, hydroxypropyl methylcellulose, polysorbate 80, sodium citrate dihydrate, sodium chloride and purified, water. The composition may contain sodium hydroxide and/or hydrochloric acid to adjust the pH to be in the range of 5.5 to 6.6.

The antibiotic/steroid ophthalmic compositions described above, particularly those in which the antibiotic is tobramycin, are ideal combinations for treating patients with ocular trauma and patients requiring control of both inflammation and infection, such as those with blepharitis, bacterial conjunctivitis and peripheral ulcerative keratitis. The antibiotic/steroid combination of the invention is typically administered four times daily over the course of two weeks for blepharitis; then, patients are maintained on formulations of the invention which do not contain the antibiotic, administered less frequently (for example from twice per day to once per week).

Another sterile ophthalmic suspension formulation contains, per mL: as active, loteprednol etabonate 2 mg (0.2%); as synergist, 11-deoxyhydrocortisone 0.1 to 0.2 mg; as preservative, benzalkonium chloride 0.01%; as inactives, edetate disodium, glycerin, povidone, purified water and tyloxapol. Hydrochloric acid and/or sodium hydroxide may be added to adjust, the pH to 5.3 to 5.6. Among other ophthalmic uses, treatment of dry eye syndrome can utilize this suspension formulation.

Yet another sterile ophthalmic suspension formulation contains, per mL: as active ingredient, loteprednol etabonate 5 mg (0.5%); as synergist, hydrocortisone acetate 0.1 to 0.5 mg; as preservative, benzalkonium chloride 0.01%; as inactive ingredients, edetate disodium, glycerine, povidone, purified water and tyloxapol Hydrochloric acid and/or sodium hydroxide may be added to adjust the pH to 5.3 to 5.6. Again, such a suspension is of use in treating dry eye syndrome.

For dermatological use, in the treatment of fungal infections with associated inflammation, a cream or lotion combining clotrimazole, a synthetic antifungal agent, a compound of formula (I) and a compound of formula (II) may be formulated. A suitable cream, or lotion contains, in each gram of cream or lotion: 10 mg of clotrimazole, 0.5 mg of loteprednol etabonate and 0.1 to 0.5 mg of hydrocortisone, in a hydrophilic cream or lotion base consisting of purified water, mineral oil, white petrolatum, cetearyl alcohol 70/30, ceteareth-30, propylene glycol, sodium phosphate monobasic monohydrate and phosphoric acid, with benzyl alcohol as a preservative. If necessary, the lotion may contain sodium hydroxide.

Capsules or tablets suitable for oral administration in the treatment of Crohn's disease may be formulated to protect the compounds of formulas (I) and (II) from gastric juice and to dissolve when they reach a higher pH in the duodenum. In one formulation of this type, each capsule contains 5-20 mg of micronized loteprednol etabonate, 2-10 mg of micronized hydrocortisone, with ethyl cellulose, acetyl tributyl citrate, methacrylic acid copolymer type C, triethyl citrate, anti foam. M, polysorbate 80, talc and sugar spheres, in a shell composed of gelatin, iron oxide and titanium oxide. The granules in the formulation are coated to prevent dissolution in gastric juice but dissolve at pH>5.5, normally when the granules reach the duodenum. After that, a matrix of ethyl cellulose with the steroids releases them in a time-dependent manner in the intestinal lumen.

For the treatment of asthma, a sterile suspension for oral inhalation via a compressed air-driven jet nebulizer may be formulated. The suspension contains, as the active ingredient, micronized loteprednol etabonate; as the enhancing agent, micronized hydrocortisone or hydrocortisone acetate (in a 0.2:1 to 1:1 weight ratio to loteprednol etabonate); and as inactives, disodium edetate, sodium chloride, sodium citrate, citric acid, polysorbate 80, and water for injection. Single dose ampules contain 0.5, 1.0, 1.5 and 2.0 mg of loteprednol etabonate.

An alternate preparation for the treatment of asthma is an inhalation-driven multidose dry powder inhaler containing only micronized loteprednol etabonate and micronized hydrocortisone. Each actuation is designed to provide 400 meg of loteprednol etabonate and about 250 meg of hydrocortisone and to act directly on the respiratory tract.

For the treatment and management of nasal symptoms of seasonal or perennial allergic rhinitis, a nasal spray or gel may be used. One such nasal foundation is a metered-dose, manual pump spray containing a micronized suspension of loteprednol etabonate and hydrocortisone acetate in an aqueous medium. The medium also contains microcrystalline cellulose and carboxymethyl cellulose sodium, anhydrous dextrose, polysorbate 80, disodium edetate, potassium sorbate and purified water, with hydrochloric acid added to adjust the pH to about 4.5. The formulation is designed to deliver 50 or 100 meg of loteprednol etabonate and 25-100 meg, respectively, of hydrocortisone acetate per spray.

To treat the pruritic and inflammatory manifestations of anti-inflammatory steroid-responsive dermatoses, especially localized lesions which are dry and scaly, a tape containing the active ingredient and enhancer may be used as both a vehicle and an occlusive dressing. One such product is a moisture-impervious plastic surgical tape containing loteprednol etabonate and hydrocortisone. Each square centimeter of tape contains 10 μg of loteprednol etabonate and 2 to 5 μg of hydrocortisone evenly distributed in the adhesive layer. The tape is made of polyethylene film, while the adhesive is a synthetic copolymer of acrylate ester and acrylic acid.

For the treatment of ulcerative colitis, a rectal suspension in a disposable single-dose enema may be formulated for ready self-administration. A typical disposable single dose unit for rectal administration contains 60 mL of suspension containing: 10-100 mg of loteprednol etabonate and 5-100 mg of hydrocortisone (in a 0.5:1 or 1:1 weight ratio to loteprednol etabonate) in air aqueous solution containing carbonier 934P, polysorbate 80, purified water, sodium hydroxide and methyl paraben For the treatment of superficial bacterial infections of the external auditory canal and treatment of infections of mastoidectomy and fenestration cavities accompanied by inflammation, an otic suspension may be used. One such suspension contains colistin sulfate and neomycin sulfate as antibiotics, the selected steroids of formulas (I) and (II) and thonzonium bromide, a surface-active agent; for example, a suspension which contains, per mL: colistin base activity, 3 mg (as the sulfate); neomycin base activity, 3.3 mg (as the sulfate); loteprednol etabonate, 10 mg (1%); hydrocortisone, 2 to 10 mg (0.2 to 1%), thonzonium bromide, 0.5 mg (0.5%), polysorbate 80, acetic acid and sodium acetate in a buffered aqueous vehicle. Thimerosal (0.002%) is added as a preservative. The suspension is buffered at pH 5.

A foam may be formulated for use in the treatment of inflammatory and pruritic manifestations of corticosteroid-responsive dermatoses of the anal region. An exemplary foam contains 1% loteprednol etabonate, 0.2 to 1% hydrocortisone, and 1% pramoxine hydrochloride (a local anaesthetic) in a hydrophilic base containing cetyl alcohol, emulsifying wax, methyl, paraben, polyoxyethylene-10 stearyl ether, propylene glycol, propyl paraben, purified water; trolamine, isobutene and propane.

For intramuscular, intrasynovial, soft tissue or intralesional injection for various conditions, especially for intrasynovial or soft, tissue injection as therapy in synovitis of osteoarthritis, rheumatoid arthritis, acute and subacute bursitis, acute gouty arthritis, epicondylitis, acute nonspecific tenosynovitis and post-traumatic osteoarthritis, a sterile aqueous suspension may be formulated. Each mL of suspension contains 20, 40 or 80 mg/mL of loteprednol etabonate; and 10, 20 or 40 or 20, 40 or 80 mg/mL, respectively, of hydrocortisone or hydrocortisone acetate, respectively; together with polyethylene glycol 3350, polysorbate 80, monobasic sodium phosphate, dibasic sodium phospate USP, benzyl, alcohol (as preservative), sodium chloride (to adjust tonicity) and when necessary to adjust pH to within 3.5 to 7.0, sodium hydroxide and/or hydrochloric acid For use in the treatment of in (lamed hemorrhoids, post irradiation proctitis, as an adjunct in the treatment of chronic ulcerative colitis, cryptitis, other inflammatory conditions of the anorectum and pruritus ani, suppositories may be formulated. One such suppository contains 10-25 mg loteprednol etabonate and 10-25 hydrocortisone (in a 1:1 weight ratio to the loteprednol etabonate) in a hydrogenated cocoglyceride base.

For relief of the inflammatory and pruritic manifestations of corticosteroid-responsive dermatoses of the anal region, a rectal cream may be used. An illustrative rectal cream contains 1% loteprednol etabonate, 1% hydrocortisone and 1% pramoxine hydrochloride (a topical anaesthetic) in a washable, nongreasy base containing stearic acid, cetyl alcohol, aquaphor, isopropyl palmitate, polyoxyl 40 stearate, propylene glycol, potassium sorbate 0.1%, sorbic acid 0.1%, triethanolamine, lauryl sulfate and water.

For various dermal conditions having both an inflammatory/pruritic component, and a fungal/bacterial component, a topical cream composition may be formulated to contain a compound of formula (I), a compound of formula (II) and iodoquinol (as an antifungal and antibacterial agent). An illustrative cream contains, per gram, 10 mg of loteprednol etabonate, 2 to 10 mg of hydrocortisone and 10 mg of iodoquinol in a greaseless base of purified water, propylene glycol, glyceryl monostearate SE, cholesterol and related sterols, isopropyl myristate, polysorbate 60, cetyl alcohol, sorbitan monostearate, polyoxyl 40 stearate, sorbic acid and polysorbate 20.

Another topical preparation for dermatological use in treating conditions with an inflammatory/pruritic component and a fungal/bacterial component may be formulated to contain a compound of formula (I), a compound of formula (II) and iodochlorhydroxyquin (also known as clioquinol), which has antifungal and antibacterial properties. These ingredients are, for example, formulated as a cream, ointment or lotion containing 3% iodochlorhydroxyquin, 0.5% or 1.0% loteprednol etabonate and 0.2 to 1.0% prednisolone acetate.

Dry eye, also known genetically as keratoconjunctivitis sicca (KCS), is a common opthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease, manifest dry eye complications.

The human ocular surface is normally covered by a tear film that is composed of a superficial thin lipid layer (primarily derived from meibomian gland secretions), a middle bulk aqueous layer (consisting of proteins, electrolytes, and water secreted by lacrimal glands), and the innermost mucus layer derived from mucins secreted by the ocular surface epithelial cells.

A stable tear film ensures comfort and serves as the refractive optical surface of the eye. Furthermore, the tear film serves as a barrier for the ocular surface against microbial infection and inflammation from mechanical trauma. Tear film deficiencies, referred to as dry eye, are a common clinical problem that can result from decreased secretion of tears by the lacrimal gland and/or increased evaporative loss due to a deficient lipid layer or blink abnormalities. Patients with mild dry eye complain of annoying eye irritations. Those with severe dry eye, such as Sjogren's syndrome, may experience constant and disabling eye irritation, and develop ocular surface epithelial disease and sight-threatening sterile or microbial corneal ulceration.

Corticosteroids are potent, non-specific anti-inflammatory drugs that inhibit a variety of chemotactic substances and factors that mediate capillary permeability, contraction of nonvascular smooth muscle, and vasodilatation. In addition, corticosteroids suppress inflammation by inhibiting edema, fibrin deposition, migration of leukocytes and phagocytic activity.

Topical corticosteroids are useful in a variety of ophthalmic conditions and are generally indicated for treatment of steroid-responsive inflammatory conditions of the palpebral and bulbar conjunctiva, cornea and anterior segment of the eye. Although corticosteroids are widely used as a topical agent for ocular inflammation, most possess a safety risk profile that limits their more general utility. A common risk associated with corticosteroid therapy is an elevation of intraocular pressure (IOP). In addition, chronic use of topical corticosteroids may result in the development of cataracts. The compounds of formula (I), and specifically loteprednol etabonate, are compounds designed as site-active corticosteroids that will undergo a predictable transformation to inactive metabolites. The relatively rapid metabolism of loteprednol etabonate to an inactive metabolite improves the safety profile of this corticosteroid. This characteristic of Lotemax® (loteprednol etabonate ophthalmic suspension, 0.5%) makes it an excellent candidate for use in inflammatory ocular conditions. The compositions and combinations of the present invention are likewise excellent candidates for treatment of such conditions in view of the presence of a compound of formula (I), such as loteprednol etabonate, therein.

For years it has been recognized that patients with dry eye develop pathologic changes of the ocular surface epithelial cells termed squamous metaplasia. Unreported research, suggests that this process is the result of increased proliferation, abnormal differentiation, and inflammation of the ocular surface epithelial cells. In contrast to normal cells, these metaplastic cells do not produce the mucus that normally coats the ocular surface and forms a barrier against infection and mechanical trauma. This renders the ocular surface susceptible to damage from the mild trauma of desiccation, blinking, rubbing, and foreign bodies (such as contact lenses).

Lotemax® (loteprednol etabonate ophthalmic suspension, 0.5%) was approved by the FDA in March of 1998 for use in the treatment of steroid responsive conditions. Researchers have concluded that there is an inflammatory etiology in some, if not most, cases of dry eye. Reports of clinical studies have supported the use of topical corticosteroid solutions in the treatment of patients with keratoconjunctivitis sicca. Stephen Pflugfelder, MD, introduced the diagnostic test of fluorescein tear clearance to further differentiate and select patients with dry eye with an inflammatory component. It is postulated that the reduced flow of tears through the tear film and out of the cul-de-sac into the naso-lacrimal duct results in stasis, which allows inflammatory mediators in the tear film to remain in contact with the mucosa of the conjunctiva and the corneal epithelium. Stasis, thus, may increase the inflammation associated with the KCS. This process may also be responsible for a further reduction of tear production in such patients.

Basic and clinical research performed over the past decade and more indicates that inflammation develops on the ocular surface as tear production and tear clearance decrease. Immunopathological changes have been observed in the conjunctiva of patients with dry eye including increased expression of immune activation and cellular adhesion molecules (e.g. HLA-DR antigen and ICAM-1) as well as infiltration of the epithelium and stroma by inflammatory cells. Increased levels of pro-inflammatory cytokines such as, IL-1, IL-6 and TNF-α, have been detected in the tear fluid and conjunctival epithelium of patients with dry eye. The fear fluid concentration of IL-1α was found to increase as tear clearance decreased. Significantly increased concentration and activity of matrix metalloproteinase-9 (MMP-9) has been detected in the tear fluid of dry eye patients with delayed tear clearance. Production of MMP-9 by corneal epithelial cells and leukocytes is stimulated by the pro-inflammatory cytokines IL-1 and TNF-α Experimental evidence suggests that MMP-9 is involved in the pathogenesis of keratoconjunctivitis sicca by dissolving the tight junction proteins that anchor the differentiated mucin-bearing apical corneal epithelial cells. Glucocorticosteroids are recognized for their ability to decrease the production of pro-inflammatory cytokines and matrix metalloproteinase enzymes. Several recent clinical studies have supported the use of topical corticosteroid solutions in the treatment of patients with keratoconjunctivitis sicca The following recent patents or publications are noted:

U.S., Pat. No. 6,153,607 discloses a preservative-free formulation containing an effective amount of a corticosteroid in an aqueous carrier to treat a dry eye condition. The formulation may be provided as a part, of a therapeutic regimen to treat a variety of dry eye conditions and ocular surface disorders manifesting delayed tear clearance previously not readily treatable. The formulation may be packaged as containers of single dosage amounts of the corticosteroid-aqueous formulation sufficient for pulsed-therapy of acute exacerbations of the irritation symptoms anti ocular surface disease of conditions associated with dry eye and delayed tear clearance.

U.S. Patent Application Publication No. 2003/0008853 discloses 22,29-epoxy-3,4,6,7,29-pentahydroxy-,(3α,4β,5α, 6α,-7β,14β,22S)-stigmastan-15-one as useful for treating dry eye disorders and other disorders requiring the wetting of the eye. This publication further notes that corticosteroids, such as prednisolone, dexamethasone, fluorometholone, hydrocortisone, loteprednol, triamcinolone, etc., cannot be used for prolonged therapy in dry eye patients without causing side effects. This publication further notes that steroid-related complications including increased intraocular pressure and cataract formation have been observed in dry eye patients treated with corticosteroids after several months of therapy. Therefore, it was surprisingly discovered that a topical ophthalmic formulation containing Loteprednol etabonate, when used for four weeks, was efficacious and well tolerated in the management of patients with KCS with inflammation. Moreover, a differential treatment effect, which was in some cases significant, was seen in subsets of patients who presented a moderate to severe inflammatory component corresponding with more severe KCS. This has been further elaborated upon in Meyerling U.S. Patent Appln. Publication No. 2005/0182039 of Aug. 18, 2005 directed to use of loteprednol etabonate for the treatment of dry eye and Bartels U.S. Patent Appln. Publication No. 2005/0222110, of Oct. 6, 2005 directed to treating moderate to severe dry eye with loteprednol etabonate, both incorporated by reference herein in their entireties and relied upon. Further, Xia et al. U.S. Patent Appln. Publication No. 2006/0148686 of Jul. 6, 2006, describes ophthalmic compositions and methods of treating dry eye wherein the composition administered is a corticosteroid, preferably loteprednol etabonate, and cyclosporin, especially Cyclosporin A; the Xia et. al. patent publication is also incorporated by reference herein in its entirety and relied upon. Other methods and combination products for treating dry eye with corticosteroids, especially with loteprednol etabonate, are described in Gamache et al. U.S. Patent Appln, Publication No. 2006/0069075, published Mar. 30, 2006 (loteprednol etabonate with a MUC-1 secretagogue such as an HETE, derivative) and Chappell et al. U.S. Patent Appln. Publication No, 2007/0105761 (loteprednol etabonate with a non-steroidal immunophilin-dependent immunosuppressant), both of which are also incorporated by reference herein in their entireties and relied upon.

Therefore, disclosed in embodiments herein is a method of treating dry eye, including moderate to severe dry eye, in patients who present an inflammatory component, especially a moderate to severe inflammatory component. Symptoms of severe dry eye may include, among others, conjunctival injection (hyperemia), such as bulbar conjunctival hyperemia, inferior tarsal conjunctival hyperemia, nasal bulbar conjunctival hyperemia; lid margin hyperemia, central corneal staining, and redness of the eye. The present method comprises topically administering to the patient with dry eye, especially moderate to severe dry eye, a combination of a compound of formula (I) and a compound of formula (II) as defined hereinabove, or a composition comprising said combination and an opthalmologically acceptable carrier, especially when the compound of formula (I) is loteprednol etabonate. In another aspect, the present invention provides compositions comprising a combination of a compound of formula (I), preferably loteprednol etabonate, and a compound of formula (II), together with cyclosporin, especially cyclosporin A, and an opthalmologically acceptable carrier. Such compositions of the invention are as discussed in detail hereinabove, except that they additionally contain cyclosporin (as disclosed for loteprednol etabonate itself by Xia et al US 2006/0148686). Alternatively, the compositions of the present invention containing (I) and (II) can be modified to include a MUC-1 secretaogue such as an HETE derivative [especially 15(S) HETE] as described by Gamache et al. US 2006/0069075 for use with loteprednol etabonate or a non-steroidal immunophilin dependent immunosuppressant as described by Chappell et al. US 2007/0105761 for use with loteprednol etabonate. Such compositions are useful in the methods of treating dry eye herein.

The present invention also contemplate methods of treating dry eye which comprise concomitantly administering the combination of compounds (I) and (II) according to the present invention with one of the additional agents mentioned in the preceding paragraph; although it is highly convenient, to place (I), (II) and the additional agent in a single dosage form, there may be instances in which separate administration is desired.

According to one method of tire present invention for treating dry eye, a formulation comprising a compound of formula (I), especially loteprednol etabonate, and a compound of formula (II) and a pharmaceutically acceptable carrier for topical ophthalmic administration or implantation into the conjunctival sac or anterior chamber of the eye is administered to a mammal in need thereof. The formulations are formulated in accordance with methods known in the art for the particular route of administration desired.

The formulations administered according to the present invention for dry eye treatment comprise a pharmaceutically effective amount of compound of formula (I), e.g. loteprednol etabonate. As used herein, a "pharmaceutically effective amount" is one which is sufficient to reduce or eliminate signs or symptoms of dry eye. Generally, for formulations intended to be administered topically to the eye in the form of eye drops or eye ointments, the amount of loteprednol etabonate will be about 0.001 to 5.0% (w/w). For preferred topically administrable ophthalmic formulations, the amount of loteprednol etabonate will be about 0.001 to 1.0% (w/w). Because of the presence of the compound/enhancer of formula (II), the amount of loteprednol etabonate can be considerably less than that required if the formula (II) compound were absent. For example, an amount of 0.2% w/w loteprednol etabonate together with an enhancer of formula (II) may afford results similar to 0.5% w/w loteprednol etabonate without the enhancer.

The formulations administered to treat dry eye according to the present invention may also include various other ingredients, including but not limited to surfactants, tonicity agents, buffers, preservatives, co-solvents and viscosity building agents.

Surfactants that can be used are surface-active agents that are acceptable for ophthalmic or otolaryngological uses. Useful surface active agents include but are not limited to polysorbate 80, tyloxapol, TWEEN 80 (ICI America Inc., Wilmington, Del.), PLURONIC F-68 (from BASF, Ludwigshafen, Germany) and the poloxamer surfactants can also be used. These surfactants are nonionic alkaline oxide condensates of an organic compound which contains hydroxyl groups. The concentration in which the surface active agent may be used is only limited by neutralization of the bactericidal effects on the accompanying preservatives (it present), or by concentrations which may cause irritation.

Various tonicity agents may be employed to adjust, the tonicity of tire formulation. For example, sodium chloride, potassium chloride, magnesium chloride, calcium chloride, nonionic diols, preferably glycerol, dextrose and/or mannitol may be added to the formulation to approximate physiological tonicity. Such an amount of tonicity agent will vary, depending on the particular agent to be added. In general, however, the formulations will have a tonicity agent in an amount sufficient to cause the final formulation to have an ophthalmically acceptable osmolality (generally about 150-450 mOsm)

An appropriate buffer system (e.g., sodium phosphate, sodium acetate, sodium citrate, sodium borate or boric acid) may be added to the formulations to prevent pH drift under storage conditions. The particular concentration will vary, depending on the agent employed.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/w Unit dose formulations of the present invention will be sterile, but typically unpreserved. Such formulations, therefore, generally will not contain preservatives Co-solvents and viscosity building agents may be added to the formulations to improve the characteristics of the formulations. Such materials can include nonionic water-soluble polymer. Other compounds designed to lubricate, "wet," approximate the consistency of endogenous tears, aid in natural tear build-up, or otherwise provide temporary relief of dry eye symptoms and conditions upon ocular administration to the eye are known in the art. Such compounds may enhance the viscosity of the formulation, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940 and carbomer 974P. Other compounds may also be added to the ophthalmic formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Formulations formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous formulations which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of loteprednol etabonate and its enhancing agent. Examples of artificial tears formulations useful as artificial fears carriers include, but are not limited to, commercial products, such as Moisture Eyes™ Lubricant Eye Drops/Artificial Tears, Moisture Eyes™ Liquid Gel lubricant eye drops, Moisture Eyes™ Preservative Free Lubricant Eye props/Artificial Tears and Moisture Eyes™ Liquid Gel Preservative Free Lubricant Eye props/Artificial Tears (Bausch & Lomb Incorporated, Rochester, N.Y.), Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al), U.S. Pat. No. 5,578,586 (Glonek et al), the contents of each of which are incorporated by reference herein.

Formulations formulated for the treatment of dry eye-type diseases and disorders may be prepared as ophthalmic ointments. Ointments are well known ophthalmic formulations and are essentially an oil-based delivery vehicle. Typical ointments use petroleum and/or lanolin base to which is added the active ingredient, usually as 0.1 to 2%, and excipients. Common bases include mineral oil, petrolatum and combinations thereof, but oil bases are not limited thereto.

The preferred formulations of the present invention are intended for administration to a human or veterinary patient suffering from dry eye or symptoms of dry eye. Preferably, such formulations will be administered topically. In general, the doses used for the above described purposes will vary, but will be in an effective amount to eliminate or improve dry eye conditions. Generally, 1-2 drops of such formulations will be administered from once to many times per day. The formulation can be provided as a package for the treatment of dry eye; the package would then include the pharmaceutical formulation comprising loteprednol etabonate and formula (II) compound contained in a pharmaceutically acceptable container; a written package insert containing instructions for using the formulation for the treatment of dry eye; and outer packaging identifying the pharmaceutical formulation contained therein. In certain embodiments wherein the formulation is preservative lice, the package would contain a pharmaceutically acceptable container suitable for single use by a user of the packaged formulation. In such embodiments it is envisioned that the outer packaging would contain at least one pharmaceutically acceptable container containing the loteprednol etabonate and compound (II) formulation. Preferably the outer packing would contain a multiplicity of single use containers, for example, enough single use containers to provide for a one-month supply of the formulation.

The methods of treating dry eye in accord, with the present invention are of particular interest in treating moderate to severe dry eye, most especially when it is associated with refractive surgery. Ideally, administration is carried out for a period of greater than one month and may even be continued for a period of greater than three year in light of studies noted in Bartels US 2005/0222110, as well as in light, of the fact that the compound of formula (II) is present in a subtherapeutic amount and therefore would not suffer from the dangers of long-term use of the formula (II) compounds in therapeutic amounts.

As noted hereinabove, cortienic acid, the corresponding $\Delta^{1,4}$ acid, and their simple alkyl esters have been previously described as enhancing the anti-inflammatory activity and duration of action of loteprednol and related soft steroids in Bodor United States Patent Application Publication No 2005/0026892, published Feb. 3, 2005, incorporated by reference herein in its entirety and relied upon. As further indicated hereinabove, such inactive metabolites have also been described as enhancing the anti-inflammatory activity and duration of action of selected other corticosteroids, for example, hydrocortisone; see Bodor United States Patent Application Publication No. 2005/0020551 A1, published Jan. 2, 2005, likewise incorporated by reference herein in its entirety and relied upon. The thus-enhanced combinations and compositions incorporating the inactive metabolite enhancing agents are highly useful in the treatment of dry eye, especially moderate to severe dry eye, most especially when the active agent is loteprednol etabonate. Again, the presence of the enhancing agent may allow comparable results with less active agent, i.e. 0.2% loteprednol etabonate plus cortienic acid or its methyl or ethyl ester or $\Delta^1$-cortienic acid or its methyl or ethyl ester is expected to be approximately as effective in treating dry eye as 0.5% loteprednol etabonate alone. The enhanced combinations, compositions and methods of Bodor US 2005/0020551 are also useful in the treatment of dry eye, especially moderate to severe dry eye. Further, the inactive metabolite-enhanced combinations, compositions and methods of Bodor US 2005/0026892 and the enhanced combinations and compositions and methods of Bodor US 2005/0020551 can be modified to additionally contain/administer cyclosporin, a MUC-1 secretagogue such as an HETE derivative or a non-steroidal immunophilin-dependent immunosuppresant to treat dry eye, as described in detail hereinabove for the combinations, compositions and methods of the present invention.

While the invention has been described in terms of various preferred embodiments, the skilled artisan will appreciate that various modifications, substitutions, omissions and changes may be made without departing from the spirit thereof. Accordingly, if is intended that the scope of the present invention be limited solely by the scope of the following claims, including equivalents thereof.

What is claimed is:

1. A method for alleviating dry eye in a warm-blooded animal exhibiting same, said method comprising administering to the eye or eyes of said animal a composition comprising:
   (a) loteprednol etabonate; and
   (b) a compound having the formula:

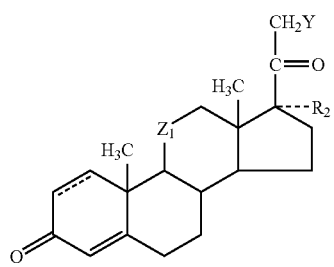

(II)

wherein:
   $Z_1$ is β-hydroxymethylene or methylene;
   $R_2$ is H or —OH;
   Y is —OH or —OCOR$_4$, wherein R$_4$ is C$_1$ alkyl;
   and the dotted line in ring A indicates that the 1,2-linkage is saturated or unsaturated;
   the compound of formula (II) being selected from the group consisting of hydrocortisone, hydrocortisone acetate, prednisolone, prednisolone acetate, corticosterone, corticosterone 21-acetate, 11 deoxycorticosterone and 11-deoxyhydrocortisone;
   in a combined synergistic anti-inflammatory effective amount;
   the amount of compound of formula (II) being sufficient to enhance the anti-inflammatory activity or duration of action, or both, loteprednol etabonate, said amount of said compound of formula (II) being insufficient alone to have anti-inflammatory activity;
   wherein the molar ratio of the compound of formula (II) to loteprednol etabonate is from about 2:1 to about 0.05:1;
   with the proviso that the composition excludes any compound having the formula:

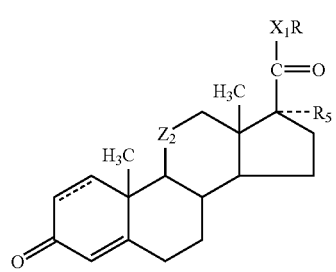

(III)

wherein:
   R is H or C$_1$—C$_4$ alkyl;
   $Z_2$ is carbonyl or β-hydroxymethylene;
   $X_1$ is —O— or —S—;
   $R_5$ is —OH, —OR$_6$, —OCOOR$_6$ or —OCOR$_7$ wherein R$_6$ is C$_1$-C$_4$ alkyl and R$_7$ is C$_1$-C$_4$ alkyl, fluoromethyl or chloromethyl;
   and the dotted line is defined as above;
   with the proviso that when R is C$_1$-C$_4$ alkyl, then R$_5$ is —OH.

2. A method according to claim 1, wherein the animal is in need of treatment to alleviate moderate to severe dry eye.

3. A method for alleviating dry eye in a warm-blooded animal exhibiting same, said method comprising administering to the eye or eyes of said animal a pharmaceutical composition comprising:
   (1) a combined synergistic anti-inflammatory effective amount of:
      (a) loteprednol etabonate; and
      (b) a compound having the formula:

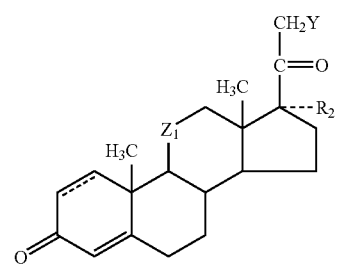

(II)

wherein $Z_1$ is β-hydroxymethylene or methylene; $R_2$ is H or —OH; Y is —OH or —OCOR$_4$ wherein R$_4$ is C$_1$ alkyl; and the dotted line in ring A indicates that the 1,2-linkage is saturated or unsaturated, the compound of formula (II) being selected from the group consisting of hydrocortisone, hydrocortisone acetate, prednisolone, prednisolone acetate, corticosterone, corticosterone 21-acetate, 11-deoxycorticosterone and 11-deoxyhydrocortisone, the amount of compound of formula (II) being sufficient to enhance the anti-inflammatory activity or duration of action, or both, of loteprednol etabonate, said amount of said compound of formula (II) being insufficient alone to have anti-inflammatory activity;
      wherein the molar ratio of the compound of formula (II) to loteprednol etabonate is from about 2:1 to about 0.05:1; and
   (2) a non-toxic, pharmaceutically acceptable carrier therefor suitable for ophthalmic application;

with the proviso that the composition excludes any compound having the formula:

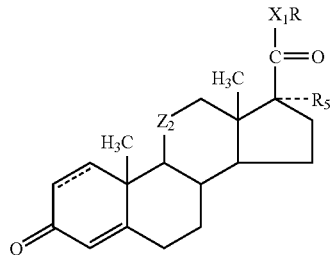

(III)

wherein:
R is H or $C_1$—$C_4$ alkyl;
$Z_2$ is carbonyl or β-hydroxymethylene;
$X_1$ is —O— or —S—;
$R_5$ is —OH, —$OR_6$, —$OCOOR_6$ or —$OCOR_7$ wherein $R_6$ is $C_1$-$C_4$ alkyl and $R_7$ is $C_1$-$C_4$ alkyl, fluoromethyl or chloromethyl;
and the dotted line is defined as above;
with the proviso that when R is $C_1$-$C_4$ alkyl, then $R_5$ is —OH.

4. A method according to claim 3, wherein the animal has moderate to severe dry eye.

5. A method according to claim 3, wherein the animal is treated for a period of greater than one month.

6. A method according to claim 5, wherein the treatment is for a period of greater than three years.

7. A method according to claim 3, wherein the composition further comprises cyclosporin.

8. A method according to claim 3, wherein the composition further comprises a MUC-1 secretagogue or a non-steroidal immunophilin-dependent immunosuppressant.

9. A method according to claim 1, wherein the molar ratio of compound of formula (II) to loteprednol etabonate is from about 1:1 to about 0.2:1.

10. A method according to claim 1, wherein the molar ratio of compound of formula (II) to loteprednol etabonate is from about 1:1 to about 0.5:1.

11. A method according to claim 3, wherein the molar ratio of compound of formula (II) to loteprednol etabonate is from about 1:1 to about 0.2 to 1.

12. A method according to claim 3, wherein the molar ratio of compound of formula (II) to loteprednol etabonate is from about 1:1 to about 0.5:1.

13. A method according to claim 7, wherein the molar ratio of compound of formula (II) to loteprednol etabonate is from about 1:1 to about 0.2:1.

14. A method according to claim 7, wherein the molar ratio of compound of formula (II) to loteprednol etabonate is from about 1:1 to about 0.5:1.

15. A method according to claim 8, wherein the molar ratio of compound of formula (II) to loteprednol etabonate is from about 1:1 to about 0.2:1.

16. A method according to claim 8, wherein the molar ratio of compound of formula (II) to loteprednol etabonate is from about 1:1 to about 0.5:1.

* * * * *